US009038633B2

(12) United States Patent
Milne et al.

(10) Patent No.: US 9,038,633 B2
(45) Date of Patent: May 26, 2015

(54) VENTILATOR-INITIATED PROMPT REGARDING HIGH DELIVERED TIDAL VOLUME

(75) Inventors: Gary Milne, Louisville, CO (US); Kirk Hensley, Dublin, OH (US); Peter R. Doyle, Vista, CA (US); Gardner Kimm, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 1120 days.

(21) Appl. No.: 13/039,020

(22) Filed: Mar. 2, 2011

(65) Prior Publication Data
US 2012/0226444 A1 Sep. 6, 2012

(51) Int. Cl.
*A61M 16/00* (2006.01)
*A62B 7/00* (2006.01)
(Continued)

(52) U.S. Cl.
CPC .............. *A61M 16/0051* (2013.01); *A61B 5/08* (2013.01); *A61M 2205/13* (2013.01);
(Continued)

(58) Field of Classification Search
CPC ............ A61M 16/00; A61M 16/0003; A61M 16/0051; A61M 2230/40; A61M 2230/42; A61M 2230/46; A61M 2205/502; A61M 2205/505; A61M 2205/507; A61M 2205/52
USPC ............................. 128/200.24, 204.18–205.26
See application file for complete search history.

(56) References Cited

U.S. PATENT DOCUMENTS

| 4,546,770 A | 10/1985 | Schlessinger et al. |
| 4,752,089 A | 6/1988 | Carter |

(Continued)

FOREIGN PATENT DOCUMENTS

| EP | 0901798 | 3/1999 |
| EP | 1449558 | 8/2004 |

(Continued)

OTHER PUBLICATIONS

Egan's Fundamentals of Respiratory Care (2003) 8$^{th}$ Edition, Editors Robert L. Wilkins, James K. Stoller and Craig L. Scanlan, p. 996.
(Continued)

*Primary Examiner* — Valerie L Skorupa
(74) *Attorney, Agent, or Firm* — Merchant & Gould P.C.

(57) ABSTRACT

This disclosure describes systems and methods for monitoring and evaluating ventilatory data to provide useful notifications and/or recommendations. Indeed, many clinicians may not easily identify or recognize data patterns and correlations indicative of certain patient conditions or the effectiveness of ventilatory treatment. Further, clinicians may not readily determine appropriate adjustments that may address certain patient conditions or the effectiveness of ventilatory treatment. Specifically, clinicians may not readily detect or recognize the occurrence of high-delivered $V_T$, during various types of ventilation. According to embodiments, a ventilator may be configured to monitor and evaluate diverse ventilatory parameters to detect an occurrence of and potential causes for high-delivered $V_T$, and may subsequently issue suitable notifications and/or recommendations. The suitable notifications and/or recommendations may further be provided in a hierarchical format such that the clinician may selectively access information regarding the high-delivered $V_T$, and/or potential causes for the high-delivered $V_T$.

20 Claims, 6 Drawing Sheets

(51) Int. Cl.
*A62B 9/00* (2006.01)
*A61B 5/08* (2006.01)
*G06F 19/00* (2011.01)
*A61B 5/00* (2006.01)
*A61B 5/0205* (2006.01)
*A61B 5/087* (2006.01)
*A61B 5/091* (2006.01)

(52) U.S. Cl.
CPC ..... *A61M 2205/18* (2013.01); *A61M 2205/505* (2013.01); *A61M 2205/581* (2013.01); *A61M 2205/583* (2013.01); *G06F 19/3406* (2013.01); *A61B 5/0205* (2013.01); *A61B 5/087* (2013.01); *A61B 5/091* (2013.01); *A61B 5/4836* (2013.01); *G06F 19/3481* (2013.01)

(56) References Cited

U.S. PATENT DOCUMENTS

| | | |
|---|---|---|
| 4,917,080 A | 4/1990 | Bayerlein |
| 4,921,642 A | 5/1990 | LaTorraca |
| 4,954,799 A | 9/1990 | Kumar |
| 5,057,822 A | 10/1991 | Hoffman |
| 5,072,737 A | 12/1991 | Goulding |
| 5,150,291 A | 9/1992 | Cummings et al. |
| 5,161,525 A | 11/1992 | Kimm et al. |
| 5,237,987 A | 8/1993 | Anderson et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,319,540 A | 6/1994 | Isaza et al. |
| 5,325,861 A | 7/1994 | Goulding |
| 5,333,606 A | 8/1994 | Schneider et al. |
| 5,335,654 A | 8/1994 | Rapoport |
| 5,339,807 A | 8/1994 | Carter |
| 5,343,857 A | 9/1994 | Schneider et al. |
| 5,351,522 A | 10/1994 | Lura |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,682 A | 3/1995 | Lynn |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,429,123 A | 7/1995 | Shaffer et al. |
| 5,438,980 A | 8/1995 | Phillips |
| 5,443,075 A | 8/1995 | Holscher |
| 5,490,502 A | 2/1996 | Rapoport et al. |
| 5,513,631 A | 5/1996 | McWilliams |
| 5,517,983 A | 5/1996 | Deighan et al. |
| 5,520,071 A | 5/1996 | Jones |
| 5,520,192 A | 5/1996 | Kitney et al. |
| 5,524,615 A | 6/1996 | Power |
| 5,531,221 A | 7/1996 | Power |
| 5,542,415 A | 8/1996 | Brady |
| 5,544,674 A | 8/1996 | Kelly |
| 5,549,106 A | 8/1996 | Gruenke et al. |
| 5,596,984 A | 1/1997 | O'Mahony et al. |
| 5,598,838 A | 2/1997 | Servidio et al. |
| 5,605,151 A | 2/1997 | Lynn |
| 5,630,411 A | 5/1997 | Holscher |
| 5,632,270 A | 5/1997 | O'Mahony et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,669,379 A | 9/1997 | Somerson et al. |
| 5,671,767 A | 9/1997 | Kelly |
| 5,672,041 A | 9/1997 | Ringdahl et al. |
| 5,673,689 A | 10/1997 | Power |
| 5,678,539 A | 10/1997 | Schubert et al. |
| 5,715,415 A | 2/1998 | Dazey et al. |
| 5,715,812 A | 2/1998 | Deighan et al. |
| 5,752,509 A | 5/1998 | Lachmann et al. |
| 5,762,480 A | 6/1998 | Adahan |
| 5,771,884 A | 6/1998 | Yarnall et al. |
| 5,791,339 A | 8/1998 | Winter |
| 5,794,986 A | 8/1998 | Gansel et al. |
| 5,803,066 A | 9/1998 | Rapoport et al. |
| 5,813,399 A | 9/1998 | Isaza et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,881,717 A | 3/1999 | Isaza |
| 5,881,723 A | 3/1999 | Wallace et al. |
| 5,884,623 A | 3/1999 | Winter |
| 5,891,023 A | 4/1999 | Lynn |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,921,920 A | 7/1999 | Marshall et al. |
| 5,927,274 A | 7/1999 | Servidio et al. |
| 5,931,160 A | 8/1999 | Gilmore et al. |
| 5,934,274 A | 8/1999 | Merrick et al. |
| 5,957,129 A | 9/1999 | Tham et al. |
| 5,964,220 A | 10/1999 | Boussignac et al. |
| 6,024,089 A | 2/2000 | Wallace et al. |
| 6,041,780 A | 3/2000 | Richard et al. |
| 6,047,860 A | 4/2000 | Sanders |
| 6,067,022 A | 5/2000 | Laswick et al. |
| 6,076,523 A | 6/2000 | Jones et al. |
| 6,116,240 A | 9/2000 | Merrick et al. |
| 6,116,464 A | 9/2000 | Sanders |
| 6,123,073 A | 9/2000 | Schlawin et al. |
| 6,135,106 A | 10/2000 | Dirks et al. |
| 6,142,150 A | 11/2000 | O'Mahoney et al. |
| 6,148,814 A | 11/2000 | Clemmer et al. |
| 6,158,430 A | 12/2000 | Pfeiffer et al. |
| 6,158,432 A | 12/2000 | Biondi et al. |
| 6,161,539 A | 12/2000 | Winter |
| 6,192,876 B1 | 2/2001 | Denyer et al. |
| 6,206,001 B1 | 3/2001 | Garber et al. |
| 6,206,837 B1 | 3/2001 | Brugnoli |
| 6,220,245 B1 | 4/2001 | Takabayashi et al. |
| 6,223,064 B1 | 4/2001 | Lynn et al. |
| 6,240,920 B1 | 6/2001 | Ström |
| 6,269,812 B1 | 8/2001 | Wallace et al. |
| 6,273,444 B1 | 8/2001 | Power |
| 6,283,119 B1 | 9/2001 | Bourdon |
| 6,305,372 B1 | 10/2001 | Servidio |
| 6,305,373 B1 | 10/2001 | Wallace et al. |
| 6,321,748 B1 | 11/2001 | O'Mahony |
| 6,322,502 B1 | 11/2001 | Schoenberg et al. |
| 6,325,785 B1 | 12/2001 | Babkes et al. |
| 6,342,039 B1 | 1/2002 | Lynn et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,398,728 B1 | 6/2002 | Bardy |
| 6,412,483 B1 | 7/2002 | Jones et al. |
| 6,439,229 B1 | 8/2002 | Du et al. |
| 6,463,930 B2 | 10/2002 | Biondi et al. |
| 6,467,478 B1 | 10/2002 | Merrick et al. |
| 6,546,930 B1 | 4/2003 | Emerson et al. |
| 6,551,243 B2 | 4/2003 | Bocionek et al. |
| 6,553,991 B1 | 4/2003 | Isaza |
| 6,557,553 B1 | 5/2003 | Borrello |
| 6,564,797 B1 | 5/2003 | Mechlenburg et al. |
| 6,569,095 B2 | 5/2003 | Eggers |
| 6,571,795 B2 | 6/2003 | Bourdon |
| 6,578,575 B1 | 6/2003 | Jonson |
| 6,584,973 B1 | 7/2003 | Biondi et al. |
| 6,609,016 B1 | 8/2003 | Lynn |
| 6,622,726 B1 | 9/2003 | Du |
| 6,644,310 B1 | 11/2003 | Delache et al. |

(56) References Cited

U.S. PATENT DOCUMENTS

| | | |
|---|---|---|
| 6,644,312 B2 | 11/2003 | Berthon-Jones et al. |
| 6,668,824 B1 | 12/2003 | Isaza et al. |
| 6,668,829 B2 | 12/2003 | Biondi et al. |
| 6,675,801 B2 | 1/2004 | Wallace et al. |
| 6,709,405 B2 | 3/2004 | Jonson |
| 6,717,589 B1 | 4/2004 | Grillo et al. |
| 6,718,974 B1 | 4/2004 | Moberg |
| 6,718,975 B2 | 4/2004 | Blomberg |
| 6,725,447 B1 | 4/2004 | Gilman et al. |
| 6,739,337 B2 | 5/2004 | Isaza |
| 6,743,172 B1 | 6/2004 | Blike |
| 6,745,764 B2 | 6/2004 | Hickle |
| 6,748,252 B2 | 6/2004 | Lynn et al. |
| 6,752,150 B1 | 6/2004 | Remmers et al. |
| 6,760,608 B2 | 7/2004 | Lynn |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,804,656 B1 | 10/2004 | Rosenfeld et al. |
| 6,807,965 B1 | 10/2004 | Hickle |
| 6,814,074 B1 | 11/2004 | Nadjafizadeh et al. |
| 6,832,609 B2 | 12/2004 | Wright et al. |
| 6,845,773 B2 | 1/2005 | Berthon-Jones et al. |
| 6,860,266 B2 | 3/2005 | Blike |
| 6,866,040 B1 | 3/2005 | Bourdon |
| 6,949,073 B2 | 9/2005 | Sarel |
| 6,960,854 B2 | 11/2005 | Nadjafizadeh et al. |
| 6,986,347 B2 | 1/2006 | Hickle |
| 7,011,091 B2 * | 3/2006 | Hill et al. ............... 128/204.18 |
| 7,017,574 B2 | 3/2006 | Biondi et al. |
| 7,018,341 B2 | 3/2006 | Wright et al. |
| 7,036,504 B2 | 5/2006 | Wallace et al. |
| 7,046,254 B2 | 5/2006 | Brown et al. |
| 7,051,735 B2 | 5/2006 | Mechlenburg et al. |
| 7,066,173 B2 | 6/2006 | Banner et al. |
| 7,073,501 B2 | 7/2006 | Remmers et al. |
| 7,077,131 B2 | 7/2006 | Hansen |
| 7,081,091 B2 | 7/2006 | Merrett et al. |
| 7,081,095 B2 | 7/2006 | Lynn et al. |
| RE39,225 E | 8/2006 | Isaza et al. |
| 7,086,399 B2 | 8/2006 | Makinson et al. |
| 7,089,937 B2 | 8/2006 | Berthon-Jones et al. |
| 7,117,438 B2 | 10/2006 | Wallace et al. |
| 7,201,734 B2 | 4/2007 | Hickle |
| 7,207,945 B2 | 4/2007 | Bardy |
| 7,210,478 B2 | 5/2007 | Banner et al. |
| 7,222,623 B2 | 5/2007 | DeVries et al. |
| 7,247,154 B2 | 7/2007 | Hickle |
| 7,256,708 B2 | 8/2007 | Rosenfeld et al. |
| 7,258,670 B2 | 8/2007 | Bardy |
| 7,270,126 B2 | 9/2007 | Wallace et al. |
| 7,307,543 B2 | 12/2007 | Rosenfeld et al. |
| 7,308,894 B2 | 12/2007 | Hickle |
| 7,315,825 B2 | 1/2008 | Rosenfeld et al. |
| 7,321,862 B2 | 1/2008 | Rosenfeld et al. |
| 7,322,937 B2 | 1/2008 | Blomberg et al. |
| 7,334,578 B2 | 2/2008 | Biondi et al. |
| 7,346,846 B2 | 3/2008 | Rossi, Jr. et al. |
| 7,369,757 B2 | 5/2008 | Farbarik |
| 7,370,650 B2 | 5/2008 | Nadjafizadeh et al. |
| 7,374,535 B2 | 5/2008 | Schoenberg et al. |
| 7,395,216 B2 | 7/2008 | Rosenfeld et al. |
| 7,398,115 B2 | 7/2008 | Lynn |
| 7,428,902 B2 | 9/2008 | Du et al. |
| 7,433,827 B2 | 10/2008 | Rosenfeld et al. |
| 7,454,359 B2 | 11/2008 | Rosenfeld et al. |
| 7,454,360 B2 | 11/2008 | Rosenfeld et al. |
| 7,460,959 B2 | 12/2008 | Jafari |
| 7,467,094 B2 | 12/2008 | Rosenfeld et al. |
| 7,475,019 B2 | 1/2009 | Rosenfeld et al. |
| 7,487,773 B2 | 2/2009 | Li |
| 7,520,279 B2 | 4/2009 | Berthon-Jones |
| 7,556,038 B2 | 7/2009 | Kirby et al. |
| 7,561,912 B2 | 7/2009 | Schatz et al. |
| 7,562,657 B2 | 7/2009 | Blanch et al. |
| 7,565,905 B2 | 7/2009 | Hickle |
| 7,650,291 B2 | 1/2010 | Rosenfeld et al. |
| 7,654,802 B2 | 2/2010 | Crawford, Jr. et al. |
| 7,681,571 B2 | 3/2010 | Makinson et al. |
| 7,694,677 B2 | 4/2010 | Tang |
| 7,698,156 B2 | 4/2010 | Martucci et al. |
| 7,708,015 B2 | 5/2010 | Seeger et al. |
| 7,717,112 B2 | 5/2010 | Sun et al. |
| 7,717,113 B2 | 5/2010 | Andrieux |
| D618,356 S | 6/2010 | Ross |
| 7,778,851 B2 | 8/2010 | Schoenberg et al. |
| 7,784,461 B2 | 8/2010 | Figueiredo et al. |
| 7,802,571 B2 | 9/2010 | Tehrani |
| 7,823,588 B2 | 11/2010 | Hansen |
| 7,831,450 B2 | 11/2010 | Schoenberg et al. |
| 7,855,716 B2 | 12/2010 | McCreary et al. |
| D632,796 S | 2/2011 | Ross et al. |
| D632,797 S | 2/2011 | Ross et al. |
| 7,886,231 B2 | 2/2011 | Hopermann et al. |
| 7,886,739 B2 * | 2/2011 | Soliman et al. .......... 128/204.21 |
| 7,891,354 B2 | 2/2011 | Farbarik |
| 7,893,560 B2 | 2/2011 | Carter |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,224,636 B2 | 7/2012 | Kundert |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 2001/0004893 A1 | 6/2001 | Biondi et al. |
| 2001/0027791 A1 | 10/2001 | Wallace et al. |
| 2002/0023644 A1 | 2/2002 | Berthon-Jones |
| 2002/0026941 A1 | 3/2002 | Biondi et al. |
| 2002/0117173 A1 | 8/2002 | Lynn et al. |
| 2002/0177758 A1 | 11/2002 | Schoenberg et al. |
| 2003/0036687 A1 | 2/2003 | Schoenberg et al. |
| 2003/0106553 A1 | 6/2003 | Vanderveen |
| 2003/0121519 A1 | 7/2003 | Estes et al. |
| 2003/0140928 A1 | 7/2003 | Bui et al. |
| 2003/0141981 A1 | 7/2003 | Bui et al. |
| 2003/0153818 A1 | 8/2003 | Bocionek et al. |
| 2003/0158466 A1 | 8/2003 | Lynn et al. |
| 2003/0188748 A1 | 10/2003 | Sinderby et al. |
| 2003/0230308 A1 | 12/2003 | Linden |
| 2004/0041828 A1 | 3/2004 | Zellhoefer |
| 2004/0121767 A1 | 6/2004 | Simpson et al. |
| 2004/0167804 A1 | 8/2004 | Simpson et al. |
| 2004/0172302 A1 | 9/2004 | Martucci et al. |
| 2004/0187871 A1 * | 9/2004 | Kimmel et al. .......... 128/204.23 |
| 2004/0236240 A1 | 11/2004 | Kraus et al. |
| 2004/0244807 A1 | 12/2004 | Sun et al. |
| 2005/0016534 A1 | 1/2005 | Ost |
| 2005/0039127 A1 | 2/2005 | Davis |
| 2005/0039748 A1 | 2/2005 | Andrieux |
| 2005/0043969 A1 | 2/2005 | Sarel |
| 2005/0055242 A1 | 3/2005 | Bello et al. |
| 2005/0065817 A1 | 3/2005 | Mihai et al. |
| 2005/0112325 A1 | 5/2005 | Hickle |
| 2005/0115561 A1 * | 6/2005 | Stahmann et al. ....... 128/200.24 |
| 2005/0124866 A1 | 6/2005 | Elaz et al. |
| 2005/0133024 A1 | 6/2005 | Coifman |

(56) References Cited

U.S. PATENT DOCUMENTS

| | | |
|---|---|---|
| 2005/0139212 A1 | 6/2005 | Bourdon |
| 2005/0188991 A1 | 9/2005 | Sun et al. |
| 2005/0204310 A1 | 9/2005 | De Zwart et al. |
| 2006/0085229 A9 | 4/2006 | Rosenfeld et al. |
| 2006/0089543 A1 | 4/2006 | Kim et al. |
| 2006/0112959 A1 | 6/2006 | Mechlenburg et al. |
| 2006/0122869 A9 | 6/2006 | Rosenfeld et al. |
| 2006/0135878 A1 | 6/2006 | Wright et al. |
| 2006/0144144 A1 | 7/2006 | Seto |
| 2006/0155206 A1 | 7/2006 | Lynn |
| 2006/0155207 A1 | 7/2006 | Lynn et al. |
| 2006/0161071 A1 | 7/2006 | Lynn et al. |
| 2006/0161459 A9 | 7/2006 | Rosenfeld et al. |
| 2006/0189880 A1 | 8/2006 | Lynn et al. |
| 2006/0195041 A1 | 8/2006 | Lynn et al. |
| 2006/0201505 A1 | 9/2006 | Remmers et al. |
| 2006/0201506 A1 | 9/2006 | Makinson et al. |
| 2006/0235324 A1 | 10/2006 | Lynn |
| 2006/0237015 A1 | 10/2006 | Berthon-Jones et al. |
| 2006/0249149 A1 | 11/2006 | Meier et al. |
| 2006/0249151 A1 | 11/2006 | Gambone |
| 2006/0271409 A1 | 11/2006 | Rosenfeld et al. |
| 2006/0276701 A1 | 12/2006 | Ray |
| 2006/0294464 A1 | 12/2006 | Tokimoto et al. |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0050715 A1 | 3/2007 | Behar |
| 2007/0077200 A1 | 4/2007 | Baker |
| 2007/0093721 A1 | 4/2007 | Lynn et al. |
| 2007/0129647 A1 | 6/2007 | Lynn |
| 2007/0149860 A1 | 6/2007 | Lynn et al. |
| 2007/0163579 A1 | 7/2007 | Li et al. |
| 2007/0173702 A1 | 7/2007 | Dlugos et al. |
| 2007/0191688 A1 | 8/2007 | Lynn |
| 2007/0191697 A1 | 8/2007 | Lynn et al. |
| 2007/0199566 A1 | 8/2007 | Be'eri |
| 2007/0203415 A1 | 8/2007 | Bardy |
| 2007/0203422 A1 | 8/2007 | Bardy |
| 2007/0203423 A1 | 8/2007 | Bardy |
| 2007/0213658 A1 | 9/2007 | Hickle |
| 2007/0227537 A1 | 10/2007 | Bemister et al. |
| 2007/0232867 A1 | 10/2007 | Hansmann |
| 2007/0284361 A1 | 12/2007 | Nadjafizadeh et al. |
| 2008/0000479 A1 | 1/2008 | Elaz et al. |
| 2008/0021379 A1 | 1/2008 | Hickle |
| 2008/0041380 A1 | 2/2008 | Wallace et al. |
| 2008/0053441 A1 | 3/2008 | Gottlib et al. |
| 2008/0066752 A1 | 3/2008 | Baker et al. |
| 2008/0072896 A1 | 3/2008 | Setzer et al. |
| 2008/0072900 A1 | 3/2008 | Kenyon et al. |
| 2008/0072902 A1 | 3/2008 | Setzer et al. |
| 2008/0078390 A1 | 4/2008 | Milne et al. |
| 2008/0081974 A1 | 4/2008 | Pav |
| 2008/0083644 A1 | 4/2008 | Janbakhsh et al. |
| 2008/0086691 A1 | 4/2008 | Hopermann |
| 2008/0091117 A1 | 4/2008 | Choncholas et al. |
| 2008/0092043 A1 | 4/2008 | Trethewey |
| 2008/0092894 A1 | 4/2008 | Nicolazzi et al. |
| 2008/0097234 A1 | 4/2008 | Nicolazzi et al. |
| 2008/0200775 A1 | 8/2008 | Lynn |
| 2008/0200819 A1 | 8/2008 | Lynn et al. |
| 2008/0236582 A1 | 10/2008 | Tehrani |
| 2008/0295837 A1* | 12/2008 | McCormick et al. .... 128/204.21 |
| 2008/0314385 A1 | 12/2008 | Brunner et al. |
| 2009/0020120 A1 | 1/2009 | Schatzl et al. |
| 2009/0143694 A1 | 6/2009 | Krauss et al. |
| 2009/0149723 A1 | 6/2009 | Krauss et al. |
| 2009/0165795 A1 | 7/2009 | Nadjafizadeh et al. |
| 2009/0171176 A1 | 7/2009 | Andersohn |
| 2009/0171226 A1 | 7/2009 | Campbell et al. |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0270752 A1 | 10/2009 | Coifman |
| 2009/0275811 A1 | 11/2009 | Schatz et al. |
| 2009/0293877 A1 | 12/2009 | Blanch et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0314290 A1 | 12/2009 | Hickle |
| 2010/0011307 A1 | 1/2010 | Desfossez et al. |
| 2010/0024820 A1 | 2/2010 | Bourdon |
| 2010/0030091 A1 | 2/2010 | Fine |
| 2010/0037895 A1 | 2/2010 | Berthon-Jones et al. |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0108064 A1 | 5/2010 | Blackwell et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0192094 A1 | 7/2010 | Jeha et al. |
| 2010/0199015 A1 | 8/2010 | Martucci et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0292544 A1* | 11/2010 | Sherman et al. ............ 600/300 |
| 2010/0300446 A1 | 12/2010 | Nicolazzi et al. |
| 2011/0004489 A1 | 1/2011 | Schoenberg et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0168177 A1 | 7/2011 | Connor |

(56) References Cited

U.S. PATENT DOCUMENTS

| | | |
|---|---|---|
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0247471 A1 | 10/2012 | Masic et al. |
| 2013/0284174 A1* | 10/2013 | Sibenaller et al. ....... 128/204.23 |

FOREIGN PATENT DOCUMENTS

| | | |
|---|---|---|
| EP | 2245985 | 11/2010 |
| WO | WO 95/16484 | 6/1995 |
| WO | WO9829790 | 7/1998 |
| WO | WO 98/41267 | 9/1998 |
| WO | WO 98/41269 | 9/1998 |
| WO | WO 98/41270 | 9/1998 |
| WO | WO 98/41271 | 9/1998 |
| WO | WO9853732 | 12/1998 |
| WO | WO 99/62403 | 12/1999 |
| WO | WO 00/45882 | 8/2000 |
| WO | WO0079466 | 12/2000 |
| WO | WO 01/00264 | 1/2001 |
| WO | WO 01/00265 | 1/2001 |
| WO | WO 02/45566 | 6/2002 |
| WO | WO 02/095200 | 11/2002 |
| WO | WO 03/053503 | 7/2003 |
| WO | WO 03/102850 | 12/2003 |
| WO | WO 2004/030509 | 4/2004 |
| WO | WO 2004/069095 | 8/2004 |
| WO | WO 2004/070546 | 8/2004 |
| WO | WO 2004/070548 | 8/2004 |
| WO | WO 2004/070549 | 8/2004 |
| WO | WO 2004/070556 | 8/2004 |
| WO | WO 2004/070557 | 8/2004 |
| WO | WO 2004/070562 | 8/2004 |
| WO | WO 2004/070994 | 8/2004 |
| WO | WO 2004/070995 | 8/2004 |
| WO | WO 2004/082751 | 9/2004 |
| WO | WO 2005/050525 | 6/2005 |
| WO | WO 2005/051177 | 6/2005 |
| WO | WO 2006/012205 | 2/2006 |
| WO | WO 2007/050435 | 5/2007 |
| WO | WO 2007/085110 | 8/2007 |
| WO | WO2007145948 | 12/2007 |
| WO | WO 2008/021222 | 2/2008 |
| WO | WO 2010/011928 | 1/2010 |
| WO | WO 2010/133986 | 11/2010 |

OTHER PUBLICATIONS

Mechanical Ventilation: Physiological and Clinical Applications (2006) 4th Edition, Editors Susan P. Pilbeam and J.M. Cairo, pp. 46-47, 144, 158-160, 168-171, 178-181, 195-202, 222-225, 373-376.
Puritan Bennett 840 Ventilator System Smarter Breath Delivery information sheet by tyco Healthcare, undated, 1 page.
Tobin, M. "Principles and Practices of Mechanical Ventilation," Second Ed. McGraw Hill 2006. p. 1062.
Thille, A., et al. "Patient-Ventilator Asynchrony During Assisted Mechanical Ventilation," Intensive Care Med. (2006) 32:1515-1522.
The ARDSNET. "Ventilation with Lower Tidal Volumes as Compared with Traditional Tidal Volumes for Acute Lung Injury and the Acute Respiratory Distress Syndrome," New England Journal of Medicine, vol. 342 No. 18, May 4, 2000, pp. 1301-1308.
U.S. Appl. No. 12/775,550, Office Action mailed Feb. 14, 2013, 32 pgs.
U.S. Appl. No. 12/775,565, Office Action mailed Feb. 14, 2013, 10 pgs.
U.S. Appl. No. 12/955,523, Office Action mailed Feb. 5, 2013, 8 pgs.
Sassoon, Catherine, MD., "Triggering of the Ventilator in Patient-Ventilator Interactions", Respiratory Care, Jan. 2011, vol. 56, No. 1, pp. 39-51.
U.S. Appl. No. 12/775,550, Advisory Action mailed Apr. 12, 2013, 3 pgs.
U.S. Appl. No. 12/775,565, Advisory Action mailed Apr. 9, 2013, 3 pgs.
U.S. Appl. No. 12/827,130, Office Action mailed May 8, 2013, 15 pgs.
U.S. Appl. No. 12/827,075, Office Action mailed Apr. 23, 2013, 17 pgs.
U.S. Appl. No. 12/826,847, Office Action mailed Apr. 24, 2013, 14 pgs.
U.S. Appl. No. 12/826,828, Office Action mailed Apr. 24, 2013, 15 pgs.
U.S. Appl. No. 12/955,422, Office Action mailed Apr. 23, 2013, 27 pgs.
U.S. Appl. No. 13/035,974, Office Action mailed Mar. 29, 2013, 14 pgs.
PCT International Search Report and Written Opinion mailed Jul. 5, 2012; International Application No. PCT/US2012/027408, 13 pgs.
U.S. Appl. No. 12/775,565, Office Action mailed Jun. 13, 2013, 8 pgs.
U.S. Appl. No. 12/955,523, Notice of Allowance mailed Jul. 15, 2013, 8 pgs.
PCT International Preliminary Report on Patentability in International Application PCT/US2012/027408, mailed Sep. 3, 2013, 8 pgs.
U.S. Appl. No. 12/775,550, Office Action mailed Jul. 18, 2013, 37 pgs.
U.S. Appl. No. 12/775,565, Notice of Allowance mailed Sep. 18, 2013, 6 pgs.
U.S. Appl. No. 12/826,828, Notice of Allowance mailed Aug. 6, 2013, 4 pgs.
U.S. Appl. No. 12/826,847, Notice of Allowance mailed Aug. 5, 2013, 3 pgs.
U.S. Appl. No. 12/827,075, Notice of Allowance mailed Aug. 6, 2013, 3 pgs.
U.S. Appl. No. 12/827,130, Notice of Allowance mailed Aug. 8, 2013, 4 pgs.
U.S. Appl. No. 12/903,358, Office Action mailed Aug. 19, 2013, 15 pgs.
U.S. Appl. No. 12/955,368, Office Action mailed Aug. 2, 2013, 12 pgs.
U.S. Appl. No. 13/035,974, Office Action mailed Sep. 23, 2013, 14 pgs.
U.S. Appl. No. 12/955,422, Notice of Allowance mailed Oct. 8, 2013, 13 pgs.

(56) References Cited

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
U.S. Appl. No. 12/775,550, Office Action mailed Sep. 26, 2012, 32 pgs.
U.S. Appl. No. 12/775,565, Office Action mailed Oct. 30, 2012, 11 pgs.
U.S. Appl. No. 12/826,828, Office Action mailed Nov. 2, 2012, 17 pgs.
U.S. Appl. No. 12/826,847, Office Action mailed Nov. 2, 2012, 16 pgs.
U.S. Appl. No. 12/827,075, Office Action mailed Nov. 9, 2012, 16 pgs.
U.S. Appl. No. 12/827,130, Office Action mailed Nov. 9, 2012, 16 pgs.

* cited by examiner

VENTILATOR-INITIATED PROMPT REGARDING HIGH DELIVERED TIDAL VOLUME

A ventilator is a device that mechanically helps patients breathe by replacing some or all of the muscular effort required to inflate and deflate the lungs. In recent years, there has been an accelerated trend towards an integrated clinical environment. That is, medical devices are becoming increasingly integrated with communication, computing, and control technologies. As a result, modern ventilatory equipment has become increasingly complex, providing for detection and evaluation of a myriad of ventilatory parameters. However, due to the shear magnitude of available ventilatory data, many clinicians may not readily identify certain patient conditions and/or changes in patient condition. For example, during various types of volume or pressure ventilation, the delivered tidal volume ($V_T$) may be higher than a threshold $V_T$ setting. Even so, the difference between the delivered tidal volume ($V_T$) and the threshold $V_T$ setting may be within an acceptable range such that the ventilator does not alarm. As such, the clinician may be unaware that high-delivered $V_T$ has occurred. Indeed, high-delivered $V_T$ may occur for a variety of reasons, e.g., decreased dynamic resistance, increased dynamic compliance, increased patient effort, etc. Thus, it may not only be difficult for a clinician to identify the occurrence of high-delivered $V_T$, but it may also be difficult for the clinician to appropriately respond when potential causes for the high-delivered $V_T$ are unknown.

Indeed, clinicians and patients may greatly benefit from ventilator notifications when the ventilator detects certain patient conditions, changes in patient condition, effectiveness of ventilatory therapy, etc., based on an evaluation of available ventilatory data.

Ventilator-Initiated Prompt Regarding High-Delivered Tidal Volume

This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect or recognize the occurrence of high-delivered $V_T$ during various types of ventilation (e.g., volume control (VC) ventilation, pressure control (PC) ventilation, pressure support (PS) ventilation, volume-targeted-pressure-control (VC+), volume-targeted-pressure-support (VS) ventilation, proportional assist (PA) ventilation, etc.). According to embodiments, a ventilator may be configured to monitor and evaluate diverse ventilatory parameters to detect both the occurrence and potential causes for high-delivered $V_T$. Subsequently, the ventilator may issue suitable notifications and recommendations for addressing the high-delivered $V_T$. The suitable notifications and recommendations may further be provided in a hierarchical format such that the clinician may selectively access information regarding the occurrence of high-delivered $V_T$, information regarding potential causes for the high-delivered $V_T$, and/or information regarding one or more recommendations for addressing the high-delivered $V_T$. In more automated systems, the one or more recommendations may be automatically implemented.

According to embodiments, a ventilator-implemented method for detecting high-delivered tidal volume ($V_T$) during ventilation is provided. The method comprises receiving one or more ventilatory settings, wherein the one or more ventilatory settings include a threshold $V_T$, and collecting ventilatory data. The method further comprises processing the collected ventilatory data, wherein processing the collected ventilatory data includes determining a delivered $V_T$. The method further comprises analyzing the delivered $V_T$ by comparing the delivered $V_T$ to the threshold $V_T$ and detecting high-delivered $V_T$ upon determining that the delivered $V_T$ is greater than the threshold $V_T$. The method further includes displaying a smart prompt when high-delivered $V_T$ is detected.

According to additional embodiments, a ventilatory system for issuing a smart prompt when high-delivered $V_T$ is detected during ventilation is provided. The ventilatory system comprises at least one processor and at least one memory containing instructions that when executed by the at least one processor perform a method. The method comprises detecting high-delivered $V_T$, identifying one or more potential causes for the high-delivered $V_T$, and determining one or more recommendations for addressing the high-delivered $V_T$. The method further comprises displaying a smart prompt comprising one or more of: an alert regarding the high-delivered $V_T$; a notification message displaying the one or more potential causes for the high-delivered $V_T$; and a recommendation message displaying the one or more recommendations for addressing the high-delivered $V_T$.

According to additional embodiments, a graphical user interface for displaying one or more smart prompts corresponding to a detected condition is provided. The graphical user interface comprises at least one window and one or more elements within the at least one window. The one or more elements comprise at least one smart prompt element for communicating information regarding the detected condition, wherein the detected condition is high-delivered $V_T$.

According to additional embodiments, a ventilator processing interface for displaying a smart prompt in response to detecting high-delivered $V_T$ is provided. The ventilator processing interface comprises means for retrieving at least some ventilatory data and means for detecting the high-delivered $V_T$. The ventilator processing interface further comprises means for identifying one or more potential causes for the high-delivered $V_T$. The ventilator processing interface further comprises means for displaying the smart prompt comprising a notification message regarding the high-delivered $V_T$ and the one or more potential causes for the high-delivered $V_T$.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the claims.

BRIEF DESCRIPTION OF THE DRAWINGS

The following drawing figures, which form a part of this application, are illustrative of described technology and are

DETAILED DESCRIPTION

Although the techniques introduced above and discussed in detail below may be implemented for a variety of medical devices, the present disclosure will discuss the implementation of these techniques for use in a mechanical ventilator system. The reader will understand that the technology described in the context of a ventilator system could be adapted for use with other therapeutic equipment for alerting and advising clinicians regarding detected patient conditions.

This disclosure describes systems and methods for monitoring and evaluating ventilatory parameters, analyzing ventilatory data associated with those parameters, and providing useful notifications and/or recommendations to clinicians. Modern ventilators monitor, evaluate, and graphically represent a myriad of ventilatory parameters. However, many clinicians may not easily identify or recognize data patterns and correlations indicative of certain patient conditions, changes in patient condition, and/or effectiveness of ventilatory treatment. Further, clinicians may not readily determine appropriate ventilatory adjustments that may address certain patient conditions and/or the effectiveness of ventilatory treatment. Specifically, clinicians may not readily detect the occurrence of high-delivered $V_T$ or identify potential causes for the high-delivered $V_T$.

According to embodiments, a ventilator may be configured to monitor and evaluate diverse ventilatory parameters to detect an occurrence of high-delivered $V_T$ and may identify potential causes for the high-delivered $V_T$. Thereafter, the ventilator may issue suitable notifications regarding the occurrence of the high-delivered $V_T$ and may issue suitable recommendations based on the potential causes for the high-delivered $V_T$. The suitable notifications and recommendations may further be provided in a hierarchical format such that the clinician may selectively access information regarding the occurrence of high-delivered $V_T$, information regarding potential causes for the high-delivered $V_T$, and/or information regarding one or more recommendations for addressing the high-delivered $V_T$. In more automated systems, the one or more recommendations may be automatically implemented.

Ventilator System

Figure 1:
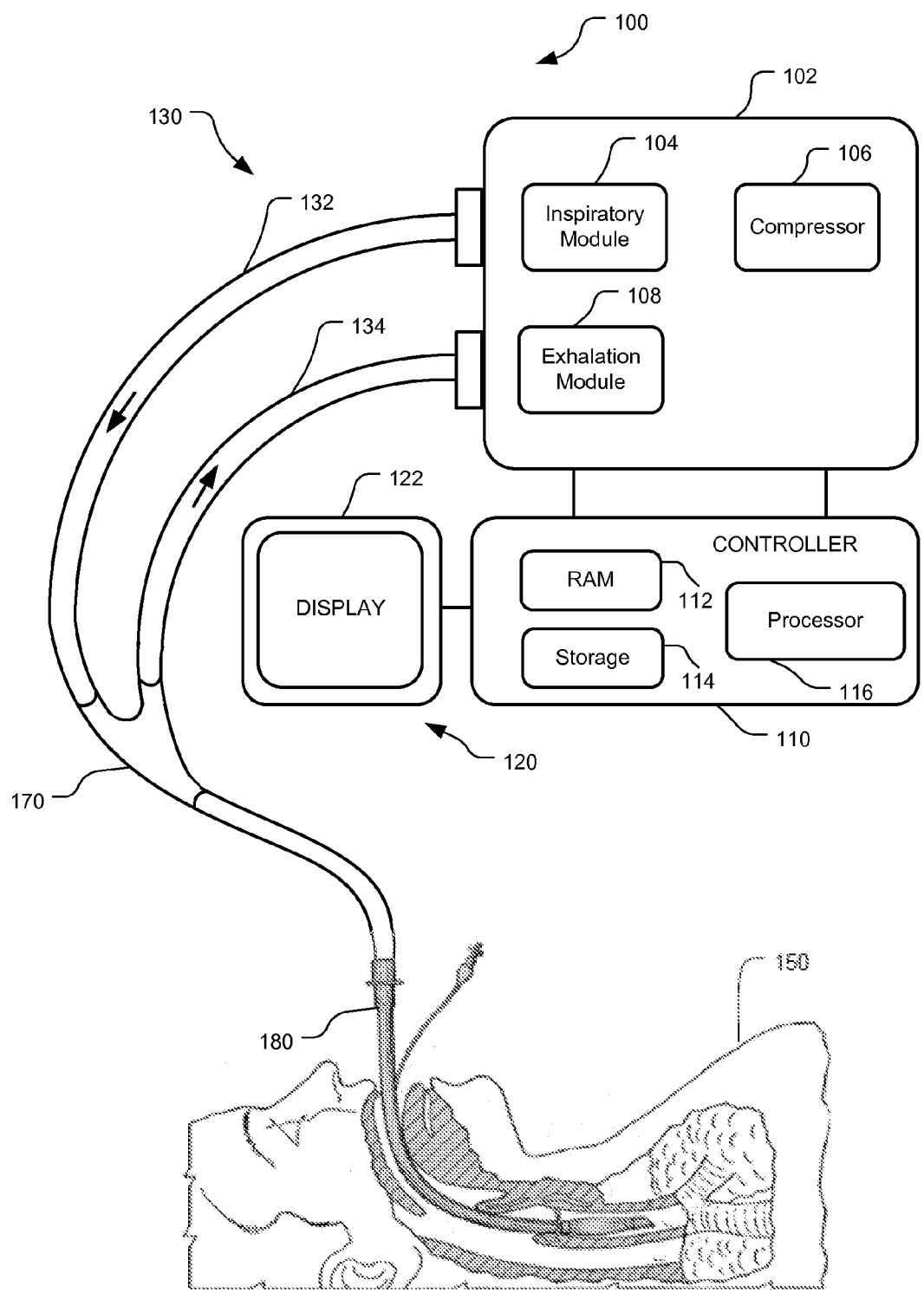
FIG. 1 is a diagram illustrating an embodiment of an exemplary ventilator connected to a human patient.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient to the pneumatic system via an invasive (e.g., endotracheal tube, as shown) or a non-invasive (e.g., nasal mask) patient interface.

Ventilation tubing system 130 may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, system 102 includes an exhalation module 108 coupled with the expiratory limb 134 and an inhalation module 104 coupled with the inspiratory limb 132. Compressor 106 or other source(s) of pressurized gases (e.g., air, oxygen, and/or helium) is coupled with inhalation module 104 to provide a gas source for ventilatory support via inspiratory limb 132.

The pneumatic system 102 may include a variety of other components, including mixing modules, valves, sensors, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). Controller 110 may include memory 112, one or more processors 116, storage 114, and/or other components of the type commonly found in command and control computing devices. In the depicted example, operator interface 120 includes a display 122 that may be touch-sensitive and/or voice-activated, enabling the display 122 to serve both as an input and output device.

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Communication between components of the ventilatory system or between the ventilatory system and other therapeutic equipment and/or remote monitoring systems may be conducted over a distributed network, as described further herein, via wired or wireless means. Further, the present methods may be configured as a presentation layer built over the TCP/IP protocol. TCP/IP stands for "Transmission Control Protocol/Internet Protocol" and provides a basic communication language for many local networks (such as intra- or extranets) and is the primary communication language for the Internet. Specifically, TCP/IP is a bi-layer protocol that allows for the transmission of data over a network. The higher layer, or TCP layer, divides a message into smaller packets, which are reassembled by a receiving TCP layer into the original message. The lower layer, or IP layer, handles addressing and routing of packets so that they are properly received at a destination.

Ventilator Components

Figure 2:
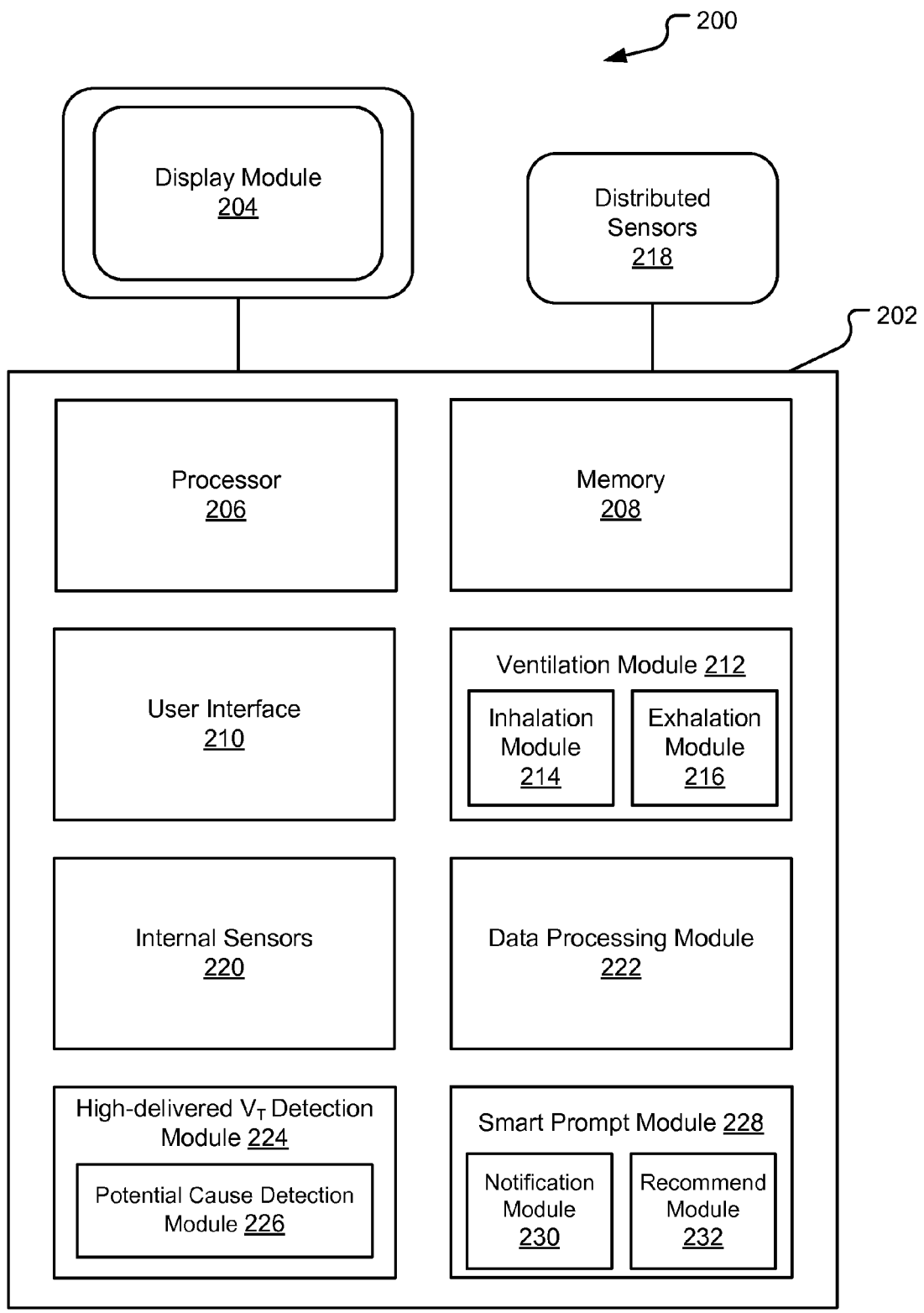
FIG. 2 is a block-diagram illustrating an embodiment of a ventilatory system for monitoring and evaluating ventilatory parameters to detect high-delivered $V_T$ and to identify potential causes for the high-delivered $V_T$.

FIG. 2 is a block-diagram illustrating an embodiment of a ventilatory system for monitoring and evaluating ventilatory parameters to detect high-delivered $V_T$ and to identify potential causes for the high-delivered $V_T$.

Ventilatory system 200 includes ventilator 202 with its various modules and components. That is, ventilator 202 may further include, inter alia, memory 208, one or more processors 206, user interface 210, and ventilation module 212 (which may further include an inspiration module 214 and an exhalation module 216). Memory 208 is defined as described above for memory 112. Similarly, the one or more processors 206 are defined as described above for one or more processors 116. Processors 206 may further be configured with a clock whereby elapsed time may be monitored by the system 200.

The ventilatory system 200 may also include a display module 204 communicatively coupled to ventilator 202. Display module 204 provides various input screens, for receiving clinician input, and various display screens, for presenting useful information to the clinician. The display module 204 is configured to communicate with user interface 210 and may include a graphical user interface (GUI). The GUI may be an interactive display, e.g., a touch-sensitive screen or otherwise, and may provide various windows (i.e., visual areas) comprising elements for receiving user input and interface command operations and for displaying ventilatory information (e.g., ventilatory data, alerts, patient information, parameter settings, etc.). The elements may include controls, graphics, charts, tool bars, input fields, smart prompts, etc. Alternatively, other suitable means of communication with the ventilator 202 may be provided, for instance by a wheel, keyboard, mouse, or other suitable interactive device. Thus, user interface 210 may accept commands and input through display module 204. Display module 204 may also provide useful information in the form of various ventilatory data regarding the physical condition of a patient and/or a prescribed respiratory treatment. The useful information may be derived by the ventilator 202, based on data collected by a data processing module 222, and the useful information may be displayed to the clinician in the form of graphs, wave representations, pie graphs, or other suitable forms of graphic display. For example, one or more smart prompts may be displayed on the GUI and/or display module 204 upon detection of high-delivered $V_T$. Additionally or alternatively, one or more smart prompts may be communicated to a remote monitoring system coupled via any suitable means to the ventilatory system 200.

Equation of Motion

Ventilation module 212 may oversee ventilation of a patient according to ventilatory settings. Ventilatory settings may include any appropriate input for configuring the ventilator to deliver breathable gases to a particular patient. Ventilatory settings may be entered by a clinician, e.g., based on a prescribed treatment protocol for the particular patient, or automatically generated by the ventilator, e.g., based on attributes (i.e., age, diagnosis, ideal body weight, gender, etc.) of the particular patient according to any appropriate standard protocol or otherwise. For example, ventilatory settings may include, inter cilia, tidal volume ($V_T$), respiratory rate (RR), inspiratory time ($T_I$), inspiratory pressure ($P_I$), pressure support ($P_{SUPP}$), rise time percent (rise time %), peak flow, flow pattern, etc.

By way of general overview, the basic elements impacting ventilation may be described by the following ventilatory equation (also known as the Equation of Motion):

$$P_m + P_v = V_T/C + R*F$$

During inspiration, $P_v$ represents the positive pressure delivered by a ventilator (generally in cm $H_2O$). $P_m$ is a measure of muscular effort that is equivalent to the pressure generated by the muscles of a patient. If the patient's muscles are inactive, the $P_m$ is equivalent to 0 cm $H_2O$. Alternatively, when the ventilator is not delivering positive pressure (i.e., $P_v=0$ cm $H_2O$), $P_m$ may be calculated according to the following formula:

$$P_m = V_T*E + R*F$$

As referenced in the above formulas, $V_T$ represents the tidal volume delivered based on the pressure supplied, C refers to the compliance, E refers to elastance, R represents the resistance, and F represents the gas flow during inspiration (generally in liters per min (L/m)). According to some embodiments, $P_m$ may be derived based on collected ventilatory data (see equation above). According to other embodiments, $P_m$ may be measured directly by various distributed pressure sensors or otherwise. According to some embodiments, the ventilator may manipulate $P_m$ data (either measured or derived) to estimate or quantify patient effort in terms of pressure (i.e., cm$H_2O$), in terms of a change in pressure over time (i.e., cm$H_2O$/s), or in terms of work (e.g., joules/liter (J/L)).

Alternatively, during exhalation, the Equation of Motion may be represented as:

$$P_a + P_t = V_{TE}/C + R*F$$

Here, $P_a$ represents the positive pressure existing in the lungs (generally in cm $H_2O$), $P_t$ represents the transairway pressure, $V_{TE}$ represents the tidal volume exhaled, C refers to the compliance, R represents the resistance, and F represents the gas flow during exhalation (generally in liters per min (L/m)).

Pressure

For positive pressure ventilation, pressure at the upper airway opening (e.g., in the patient's mouth) is positive relative to the pressure at the body's surface (i.e., relative to the ambient atmospheric pressure to which the patient's body surface is exposed, about 0 cm $H_2O$). As such, when $P_v$ is zero, i.e., no ventilatory pressure is being delivered, the upper airway opening pressure will be equal to the ambient pressure (i.e., about 0 cm $H_2O$). However, when inspiratory pressure is applied (i.e., positive pressure), a pressure gradient is created that allows gases to flow into the airway and ultimately into the lungs of a patient during inspiration (or, inhalation) until the pressure is equalized. When tidal volume ($V_T$) has been delivered to the lungs such that the inspiratory pressure is achieved and maintained, pressure is equalized and gases no longer flow into the lungs (i.e., zero flow).

Lung pressure or alveolar pressure, $P_a$, may be measured or derived. For example, $P_a$ may be measured via a distal pressure transducer or other sensor near the lungs and/or the diaphragm. Alternatively, $P_a$ may be estimated by measuring the plateau pressure, $P_{Plat}$, via a proximal pressure transducer or other sensor at or near the airway opening. Plateau pressure, $P_{Plat}$, refers to a slight plateau in pressure that is observed at the end of inspiration when inspiration is held for a period of time, sometimes referred to as an inspiratory hold or pause maneuver, or a breath-hold maneuver. That is, when inspiration is held, pressure inside the alveoli and mouth are equal (i.e., no gas flow). However, as a result of muscular relaxation and elastance of the lungs during the hold period, forces are exerted on the inflated lungs that create a positive pressure. This positive pressure is observed as a plateau in the pressure waveform that is slightly below the peak inspiratory pressure, $P_{Peak}$, prior to initiation of exhalation. As may be appreciated, for accurate measurement of $P_{Plat}$, the patient should be sedated or non-spontaneous (as muscular effort during the inspiratory pause may skew the pressure measurement). Upon determining $P_{Plat}$ based on the pressure waveform or otherwise, $P_{Plat}$ may be used as an estimate of $P_a$ (alveolar pressure).

Flow and Volume

Volume refers to the amount of gas delivered to a patient's lungs, usually in liters (L). Flow refers to a rate of change in volume over time (F=ΔV/Δt). Flow is generally expressed in liters per minute (L/m or lpm) and, depending on whether gases are flowing into or out of the lungs, flow may be referred to as inspiratory flow (positive flow) or expiratory flow (negative flow), respectively. According to embodiments, the ventilator may control the rate of delivery of gases to the patient, i.e., inspiratory flow, and may control the rate of release of gases from the patient, i.e., expiratory flow.

As may be appreciated, volume and flow are closely related. That is, where flow is known or regulated, volume may be derived based on elapsed time. For example, during volume-controlled (VC) ventilation, a tidal volume, $V_T$, may be delivered upon reaching a set inspiratory time ($T_I$) at set inspiratory flow. Alternatively, set $V_T$ and set inspiratory flow may determine the amount of time required for inspiration, i.e., $T_I$. During pressure control (PC) ventilation, pressure support (PS) ventilation, volume-targeted-pressure-control (VC+), volume-targeted-pressure-support (VS) ventilation, or proportional assist (PA) ventilation, delivered tidal volume may be determined based on integrating the flow waveform over $T_I$ (set $T_I$ in the case of PC or VC+ ventilation or patient-determined $T_I$ in the case of PS, PA, and VS ventilation). For purposes of this disclosure, the terms "set $V_T$" or "target $V_T$" are used to refer to a ventilatory setting configured to deliver a particular volume of gases to a patient's lungs. Further, set $V_T$ (or target $V_T$) may be configured by the clinician, automatically configured by the ventilator according to an appropriate protocol (e.g., based on one or more patient attributes including age, gender diagnosis, PBW or IBW), or otherwise.

Compliance

Additional ventilatory parameters that may be measured and/or derived may include compliance and resistance, which refer to the load against which the patient and/or the ventilator must work to deliver gases to the lungs. Generally, compliance refers to a relative ease with which something distends and is the inverse of elastance, which refers to the tendency of something to return to its original form after being deformed. As related to ventilation, compliance refers to the lung volume achieved for a given amount of delivered pressure (C=ΔV/ΔP). Increased compliance may be detected when the ventilator measures an increased volume relative to the given amount of delivered pressure. Some lung diseases (e.g., acute respiratory distress syndrome (ARDS)) may decrease compliance and, thus, require increased pressure to inflate the lungs. Alternatively, other lung diseases may increase compliance, e.g., emphysema, and may require less pressure to inflate the lungs.

According to embodiments, static compliance and dynamic compliance may be calculated. Static compliance, $C_S$, represents compliance impacted by elastic recoil at zero flow (e.g., of the chest wall, patient circuit, and alveoli). As elastic recoil of the chest wall and patient circuit may remain relatively constant, static compliance may generally represent compliance as affected by elastic recoil of the alveoli. As described above, $P_{Plat}$ refers to a slight plateau in pressure that is observed after relaxation of pleural muscles and elastic recoil, i.e., representing pressure delivered to overcome elastic forces. As such, $P_{Plat}$ provides a basis for estimating $C_S$ as follows:

$$C_S = V_T/(P_{Plat} - EEP)$$

Where $V_T$ refers to tidal volume, $P_{Plat}$ refers to plateau pressure, and EEP refers to end-expiratory pressure, or baseline pressure (including PEEP plus Auto-PEEP, if any), as discussed below. Note that proper calculation of $C_S$ depends on accurate measurement of $V_T$ and $P_{Plat}$.

Dynamic compliance, $C_D$, is measured during airflow and, as such, is impacted by both elastic recoil and airway resistance. Peak inspiratory pressure, $P_{Peak}$, which represents the highest pressure measured during inspiration, i.e., pressure delivered to overcome both elastic and resistive forces to inflate the lungs, is used to calculate $C_D$ as follows:

$$C_D = V_T/(P_{Peak} - EEP)$$

Where $V_T$ refers to tidal volume, $P_{Peak}$ refers to peak inspiratory pressure, and EEP refers to end-expiratory pressure. According to embodiments, the term "compliance" may generally refer to dynamic compliance unless specified. According to embodiments, ventilatory data may be more readily available for trending compliance of non-triggering patients than of triggering patients.

Resistance

Resistance refers to frictional forces that resist airflow, e.g., due to synthetic structures (e.g., endotracheal tube, exhalation valve, etc.), anatomical structures (e.g., bronchial tree, esophagus, etc.), or viscous tissues of the lungs and adjacent organs. Resistance is highly dependant on the diameter of the airway. That is, a larger airway diameter entails less resistance and a higher concomitant flow. Alternatively, a smaller airway diameter entails higher resistance and a lower concomitant flow. In fact, decreasing the diameter of the airway results in an exponential increase in resistance (e.g., two-times reduction of diameter increases resistance by sixteen times). As may be appreciated, resistance may also increase due to a restriction of the airway that is the result of, inter alia, increased secretions, bronchial edema, mucous plugs, bronchospasm, and/or kinking of the patient interface (e.g., invasive endotracheal or tracheostomy tubes).

Airway resistance may further be represented mathematically as:

$$R = P_t/F$$

Where $P_t$ refers to the transairway pressure and F refers to the flow. That is, $P_t$ refers to the pressure necessary to overcome resistive forces of the airway. Resistance may be expressed in centimeters of water per liter per second (i.e., cm $H_2O$/L/s).

Pulmonary Time Constant

As discussed above, compliance refers to the lung volume achieved for a given amount of delivered pressure (C=ΔV/ΔP). That is, stated differently, volume delivered is equivalent to the compliance multiplied by the delivered pressure (ΔV=C*ΔP). However, as the lungs are not perfectly elastic, a period of time is needed to deliver the volume ΔV at pressure ΔP. A pulmonary time constant, τ, may represent a time necessary to inflate or exhale a given percentage of the volume at delivered pressure Δ P. The pulmonary time constant, τ, may be calculated by multiplying the resistance by the compliance (τ=R*C) for a given patient and z is generally represented in seconds, s. The pulmonary time constant associated with exhalation of the given percentage of volume may be termed an expiratory time constant and the pulmonary time constant associated with inhalation of the given percentage of volume may be termed an inspiratory time constant.

According to some embodiments, when expiratory resistance data is available, the pulmonary time constant may be calculated by multiplying expiratory resistance by compliance. According to alternative embodiments, the pulmonary time constant may be calculated based on inspiratory resistance and compliance. According to further embodiments, the expiratory time, $T_E$, should be equal to or greater than a predetermined number of pulmonary time constants (e.g., about three pulmonary time constants) to ensure adequate exhalation. The predetermined number of pulmonary time constants may be selected via any suitable means, e.g., a standard protocol, an institutional protocol, clinician input, etc. According to embodiments, for a spontaneously-breathing patient, $T_E$ (e.g., determined by trending $T_E$ or otherwise) should be equal to or greater than the predetermined number of pulmonary time constants. For a non-spontaneously-breathing patient, set RR should yield a $T_E$ that is equal to or greater than the predetermined number of pulmonary time constants.

Inspiration

Ventilation module 212 may further include an inspiration module 214 configured to deliver gases to the patient according to prescribed ventilatory settings. Specifically, inspiration module 214 may correspond to the inhalation module 104 or may be otherwise coupled to source(s) of pressurized gases (e.g., air, oxygen, and/or helium), and may deliver gases to the patient. Inspiration module 214 may be configured to provide ventilation according to various ventilatory types and modes, e.g., via volume-targeted, pressure-targeted, or via any other suitable type of ventilation.

According to embodiments, the inspiration module 214 may provide ventilation via a form of volume ventilation. Volume ventilation refers to various forms of volume-targeted ventilation that regulate volume delivery to the patient. Different types of volume ventilation are available depending on the specific implementation of volume regulation. Volume ventilation may include volume-control (VC), volume-assist, or volume assist/control ventilation. Volume control (VC) ventilation may be provided by delivering a set peak flow and flow pattern for a period of time ($T_I$) to deliver a prescribed tidal volume (i.e., set $V_T$) to the patient. For non-spontaneously-breathing patients, a set $V_T$ and inspiratory time ($T_I$) may be configured during ventilation start-up, e.g., based on the patient's predicted or ideal body weight (PBW or IBW). In this case, flow will be dependent on the set $V_T$ and set $T_I$. Alternatively, set $V_T$ and a peak flow and flow pattern may be set such that $T_I$ is a function of these settings. For spontaneously-breathing patients, a set $V_T$ may be configured and the patient may determine $T_I$.

According to embodiments, during volume ventilation, as volume and flow are regulated by the ventilator, delivered $V_T$, flow waveforms (or flow traces), and volume waveforms may be constant and may not be affected by variations in lung or airway characteristics (e.g., compliance and/or resistance). Alternatively, pressure readings may fluctuate based on lung or airway characteristics. According to some embodiments, the ventilator may control the inspiratory flow and then derive volume based on integrating the inspiratory flow over elapsed time.

According to alternative embodiments, the inspiration module 214 may provide ventilation via a form of pressure ventilation. Pressure-targeted types of ventilation may be provided by regulating the pressure delivered to the patient in various ways. According to embodiments described herein, pressure support (PS) ventilation and pressure control (PC) ventilation may be accomplished by setting an inspiratory pressure ($P_I$) (or a pressure support level, $P_{SUPP}$) for delivery to the patient. Pressure ventilation may also include volume-targeted-pressure-control (VC+) or volume-targeted-pressure-support (VS) ventilation, in which a set $V_T$ is targeted by calculating and delivering an effective pressure at the patient airway. Furthermore, pressure ventilation may include proportional assist (PA) ventilation, in which a pressure is targeted that is a function of a clinician-selected percent support, PEEP, an estimate of the patient's resistance and elastance, and a calculation of tube resistance.

According to embodiments, during pressure control (PC) ventilation, the ventilator delivers mandatory breaths to a patient by "targeting" a pressure at the patient airway, which target pressure is equivalent to a set PEEP (if any) plus a set $P_I$. For example, the ventilator may increase pressure in the patient airway based on a set rise time %, which dictates how quickly the ventilator will generate the target pressure within a set $T_I$. The pressure trajectory for a PC breath type depends on the set $P_I$, set PEEP, set $T_I$, and the rise time %. In contrast, the flow-delivery profile is dependent on the rise time %, the patient's resistance and compliance, and the patient's inspiratory effort (if any). According to embodiments, during PC ventilation, the ventilator may further determine delivered $V_T$ at the end of inspiration and compare the delivered $V_T$ to a threshold $V_T$ setting.

According to alternative embodiments, during volume-targeted-pressure-control (VC+) ventilation the ventilator delivers mandatory breaths to a patient by calculating and delivering an effective pressure in the patient circuit that is projected to achieve a target tidal volume ($V_T$) within a set inspiratory time ($T_I$). More specifically, at the beginning of each breath, the ventilator may retrieve data regarding the end-inspiratory pressure (EIP), the end-expiratory pressure (EEP), and the delivered volume associated with the last breath cycle. For example, delivered volume (delivered $V_T$) may be determined based on integrating the net flow during the last inspiration and applying various volume compensations (e.g., tube compliance). Thereafter, the ventilator may utilize the retrieved data, the delivered $V_T$, and the patient's IBW or PBW to estimate the patient's compliance and may calculate a revised effective pressure for use in the next breathing cycle that is projected to deliver the set $V_T$. According to embodiments, during VC+ ventilation, the ventilator may further determine delivered $V_T$ at the end of inspiration and compare the delivered $V_T$ to a threshold $V_T$ setting.

According to alternative embodiments, during pressure support (PS) ventilation, the ventilator delivers breaths spontaneously to a patient by "targeting" a pressure at the patient airway that is equivalent to a set PEEP plus a set pressure support ($P_{SUPP}$) level. For example, upon detection of an inspiratory effort the ventilator may increase pressure in the patient airway based on a set rise time % to achieve the target pressure. The pressure trajectory for a PS breath type depends on the set $P_{SUPP}$, set PEEP, and set rise time %. In contrast, the flow-delivery profile is a function of the rise time %, the patient's resistance and compliance, and the patient's inspiratory effort. According to embodiments, during PS ventilation, the ventilator may further determine delivered $V_T$ at the end of inspiration and compare the delivered $V_T$ to a threshold $V_T$ setting.

According to alternative embodiments, during volume-targeted-pressure-support (VS) ventilation, the ventilator delivers spontaneous breaths to a patient by calculating and delivering an effective pressure in the patient circuit that is projected to achieve a set (or target) $V_T$. More specifically, at the beginning of each breath, the ventilator may retrieve data regarding the end-inspiratory pressure (EIP), the end-expiratory pressure (EEP), and the delivered volume associated with the last breath cycle. For example, delivered volume (delivered $V_T$) may be determined based on integrating the net flow during the last inspiration and applying various volume compensations (e.g., tube compliance). Thereafter, the ventilator may utilize the retrieved data, the delivered $V_T$, and the patient's IBW or PBW to estimate the patient's compliance and may calculate a revised effective pressure for use in the next breathing cycle that is projected to deliver the set $V_T$. According to embodiments, during VS ventilation, the ventilator may further determine delivered $V_T$ at the end of inspiration and compare the delivered $V_T$ to a threshold $V_T$ setting.

According to still other embodiments, during proportional assist (PA) ventilation, the ventilator delivers a target pressure to the patient airway that is a function of a clinician-selected percent support, set PEEP, an estimate of the patient's resistance and elastance, and a calculation of the tube resistance (dependent on tube type and the internal diameter of the tube). According to embodiments, during PA ventilation, the ventilator may further determine delivered $V_T$ at the end of inspiration and compare the delivered $V_T$ to a threshold $V_T$ setting.

According to further embodiments, the ventilator may be configured in various modes for delivering the various breath types. For example, in A/C mode, the ventilator may be configured to deliver VC, PC or VC+ breath types that are either initiated by the ventilator according to a set RR (e.g., ventilator-initiated-mandatory breaths or VIMs) or initiated by the patient based on detected inspiratory effort (e.g., patient-initiated-mandatory breaths or PIMs). According to an alternative example, in bi-level mode, the ventilator may alternate between high and low PEEP settings and may be configured to deliver PC, PA, or PS breath types, depending on whether the patient is spontaneously-breathing or not. Alternatively, in SIMV mode, the ventilator may be configured to deliver VC, PC or VC+ breath types during a mandatory interval (VIMs or PIMs) and to deliver either PA or PS breath types during a spontaneous interval. Alternatively still, in a spontaneous mode, the ventilator may be configured to deliver either PA or PS breath types to a spontaneously-breathing patient. Indeed, the ventilator may be configured to deliver pressure-based breaths according to any appropriate ventilatory mode or otherwise.

Exhalation

Ventilation module 212 may further include an exhalation module 216 configured to release gases from the patient's lungs according to prescribed ventilatory settings. Specifically, exhalation module 216 may correspond to exhalation module 108 or may otherwise be associated with and/or control an exhalation valve for releasing gases from the patient. By way of general overview, a ventilator may initiate exhalation based on lapse of an inspiratory time setting ($T_I$) or other cycling criteria set by the clinician or derived from ventilator settings (e.g., detecting delivery of prescribed $V_T$ or prescribed $P_I$ based on a reference trajectory). Alternatively, exhalation may be cycled based on detection of patient effort or otherwise. Upon initiating the exhalation phase, exhalation module 216 may allow the patient to exhale by opening an exhalation valve. As such, exhalation is passive, and the direction of airflow, as described above, is governed by the pressure gradient between the patient's lungs (higher pressure) and the ambient surface pressure (lower pressure). Although expiratory flow is passive, it may be regulated by the ventilator based on the size of the exhalation valve opening. Indeed, the ventilator may regulate the exhalation valve in order to target set PEEP by applying a number of calculations and/or trajectories.

For a spontaneously-breathing patient, expiratory time ($T_E$) is the time from the end of inspiration until the patient triggers the next inspiration. For a non-spontaneously-breathing patient, it is the time from the end of inspiration until the next inspiration based on the set $T_I$ and set RR. As may be further appreciated, at the point of transition between inspiration and exhalation, the direction of airflow may abruptly change from flowing into the lungs to flowing out of the lungs or vice versa depending on the transition. Stated another way, inspiratory flow may be measurable in the ventilatory circuit until $P_{Peak}$ is reached (i.e., $P_I$ plus PEEP or $P_{SUPP}$ plus PEEP), at which point flow approximates zero. Thereafter, upon initiation of exhalation, expiratory flow is measurable in the ventilatory circuit until the pressure gradient between the lungs and the body's surface reaches zero (again, resulting in zero flow). However, in some cases, expiratory flow may still be positive, i.e., measurable, at the end of exhalation (termed positive end-expiratory flow or positive EEF). In this case, positive EEF is an indication that the pressure gradient has not reached zero or, similarly, that the patient has not completely exhaled.

Ventilator Synchrony and Patient Triggering

According to some embodiments, the inspiration module 214 and/or the exhalation module 216 may be configured to synchronize ventilation with a spontaneously-breathing, or triggering, patient. That is, the ventilator may be configured to detect patient effort and may initiate a transition from exhalation to inhalation (or from inhalation to exhalation) in response. Triggering refers to the transition from exhalation to inhalation in order to distinguish it from the transition from inhalation to exhalation (referred to as cycling). Ventilation systems, depending on their mode of operation, may trigger and/or cycle automatically, or in response to a detection of patient effort, or both.

Specifically, the ventilator may detect patient effort via a pressure-monitoring method, a flow-monitoring method, direct or indirect measurement of nerve impulses, or any other suitable method. Sensing devices may be either internal or distributed and may include any suitable sensing device, as described further herein. In addition, the sensitivity of the ventilator to changes in pressure and/or flow may be adjusted such that the ventilator may properly detect the patient effort, i.e., the lower the pressure or flow change setting the more sensitive the ventilator may be to patient triggering.

According to embodiments, a pressure-triggering method may involve the ventilator monitoring the circuit pressure, as described above, and detecting a slight drop in circuit pressure. The slight drop in circuit pressure may indicate that the patient's respiratory muscles, $P_m$, are creating a slight negative pressure gradient between the patient's lungs and the airway opening in an effort to inspire. The ventilator may interpret the slight drop in circuit pressure as patient effort and may consequently initiate inspiration by delivering respiratory gases.

Alternatively, the ventilator may detect a flow-triggered event. Specifically, the ventilator may monitor the circuit flow, as described above. If the ventilator detects a slight drop in flow during exhalation, this may indicate, again, that the patient is attempting to inspire. In this case, the ventilator is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator to detect expiratory flow changes and patient triggering. For example, while gases are generally flowing out of the patient's lungs during exhalation, a drop in flow may occur as some gas is redirected and flows into the lungs in response to the slightly negative pressure gradient between the patient's lungs and the body's surface. Thus, when the ventilator detects a slight drop in flow below the bias flow by a predetermined threshold amount (e.g., 2 L/min below bias flow), it may interpret the drop as a patient trigger and may consequently initiate inspiration by delivering respiratory gases.

Ventilator Sensory Devices

The ventilatory system 200 may also include one or more distributed sensors 218 communicatively coupled to ventilator 202. Distributed sensors 218 may communicate with various components of ventilator 202, e.g., ventilation module 212, internal sensors 220, data processing module 222, high-delivered $V_T$ detection module 224, and any other suitable components and/or modules. Distributed sensors 218 may be placed in any suitable location, e.g., within the ventilatory circuitry or other devices communicatively coupled to the ventilator. For example, sensors may be affixed to the ventilatory tubing or may be imbedded in the tubing itself. According to some embodiments, sensors may be provided at or near the lungs (or diaphragm) for detecting a pressure in the lungs. Additionally or alternatively, sensors may be affixed or imbedded in or near wye-fitting 170 and/or patient interface 180, as described above.

Distributed sensors 218 may further include pressure transducers that may detect changes in circuit pressure (e.g., electromechanical transducers including piezoelectric, variable capacitance, or strain gauge) or changes in a patient's muscular pressure ($P_m$). Distributed sensors 218 may further include various flowmeters for detecting airflow (e.g., differential pressure pneumotachometers). For example, some flowmeters may use obstructions to create a pressure decrease corresponding to the flow across the device (e.g., differential pressure pneumotachometers) and other flowmeters may use turbines such that flow may be determined based on the rate of turbine rotation (e.g., turbine flowmeters). Alternatively, sensors may utilize optical or ultrasound techniques for measuring changes in ventilatory parameters. A patient's blood parameters or concentrations of expired gases may also be monitored by sensors to detect physiological changes that may be used as indicators to study physiological effects of ventilation, wherein the results of such studies may be used for diagnostic or therapeutic purposes. Indeed, any distributed sensory device useful for monitoring changes in measurable parameters during ventilatory treatment may be employed in accordance with embodiments described herein.

Ventilator 202 may further include one or more internal sensors 220. Similar to distributed sensors 218, internal sensors 220 may communicate with various components of ventilator 202, e.g., ventilation module 212, internal sensors 220, data processing module 222, high-delivered $V_T$ detection module 224, and any other suitable components and/or modules. Internal sensors 220 may employ any suitable sensory or derivative technique for monitoring one or more parameters associated with the ventilation of a patient. However, the one or more internal sensors 220 may be placed in any suitable internal location, such as, within the ventilatory circuitry or within components or modules of ventilator 202. For example, sensors may be coupled to the inhalation and/or exhalation modules for detecting changes in, circuit pressure and/or flow. Specifically, internal sensors may include pressure transducers and flowmeters for measuring changes in circuit pressure and airflow. Additionally or alternatively, internal sensors may utilize optical or ultrasound techniques for measuring changes in ventilatory parameters. For example, a patient's expired gases may be monitored by internal sensors to detect physiological changes indicative of the patient's condition and/or treatment, for example. Indeed, internal sensors may employ any suitable mechanism for monitoring parameters of interest in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors, as described above, or may be indirectly monitored by derivation according to the Equation of Motion.

Ventilatory Data

Ventilator 202 may further include a data processing module 222. As noted above, distributed sensors 218 and internal sensors 220 may collect data regarding various ventilatory parameters. A ventilatory parameter refers to any factor, characteristic, or measurement associated with the ventilation of a patient, whether monitored by the ventilator or by any other device. Sensors may further transmit collected data to the data processing module 222 and, according to embodiments, the data processing module 222 may be configured to collect data regarding some ventilatory parameters, to derive data regarding other ventilatory parameters, and/or to graphically represent collected and derived data to the clinician and/or other modules of the ventilatory system. According to embodiments, any collected, derived, and/or graphically represented data may be defined as ventilatory data. Some collected, derived, and/or graphically represented data may be indicative of delivered $V_T$. For example, delivered volume (delivered $V_T$) may be determined based on integrating the net flow during the last inspiration and applying various volume compensations (e.g., tube compliance). Furthermore, causes for a high-delivered $V_T$ may be determined based on evaluating resistance, compliance, patient effort, etc. As such, ventilatory data that may be used to calculate the delivered $V_T$, to detect high-delivered $V_T$ (e.g., based on a threshold $V_T$ setting, protocol, or otherwise), and to identify potential causes for the high-delivered $V_T$ may be collected, derived, and/or graphically represented by data processing module 222.

Flow Data

For example, according to embodiments, data processing module 222 may be configured to monitor inspiratory and expiratory flow. Flow may be measured by any appropriate, internal or distributed device or sensor within the ventilatory system. As described above, flowmeters may be employed by the ventilatory system to detect circuit flow. However, any suitable device either known or developed in the future may be used for detecting airflow in the ventilatory circuit.

Data processing module 222 may be further configured to plot monitored flow data graphically via any suitable means. For example, according to embodiments, flow data may be plotted versus time (flow waveform), versus volume (flow-volume loop), or versus any other suitable parameter as may be useful to a clinician. According to embodiments, flow may be plotted such that each breath may be independently identified. Further, flow may be plotted such that inspiratory flow and expiratory flow may be independently identified, e.g., inspiratory flow may be represented in one color and expiratory flow may be represented in another color.

As detailed above, resistance refers to frictional forces that resist airflow, e.g., due to synthetic structures (e.g., endotracheal tube, exhalation valve, etc.), anatomical structures (e.g., bronchial tree, esophagus, etc.), or viscous tissues of the lungs and adjacent organs. As may be appreciated, flow decreases as resistance increases, making it more difficult to pass gases into and out of the lungs (i.e., $F=P_t/R$). Generally, when a patient is intubated, i.e., having either an endotracheal or a tracheostomy tube in place, resistance is increased as a result of the smaller diameter of the tube over the patient's natural airway. Furthermore, resistance may be increased when secretions, such as mucus, collect in the endotracheal or tracheostomy tube. Higher resistance may necessitate, inter alia, a higher inspiratory time setting ($T_I$) for delivering a prescribed pressure or volume of gases, a higher flow setting (or rise time % for delivering prescribed pressure or volume, a lower respiratory rate resulting in a higher expiratory time ($T_E$) for complete exhalation of gases, etc.

In contrast, flow increases as resistance decreases, making it easier to pass gases (i.e., volume) into the patient's lungs for a given amount of applied pressure. Resistance may decrease for a number of reasons. For example, as resistance is dependent on the patient's anatomical structures (e.g., bronchial tree, esophagus, etc.) and the viscous tissues of the lungs and adjacent organs, changes in the condition of the patient may decrease resistance. Furthermore, when the clinician suctions the patient interface (i.e., endotracheal or tracheostomy tube), resistance may be decreased. Indeed, even changes in patient position may result in a decrease in resistance. When resistance decreases, additional tidal volume ($V_T$) may be delivered to the patient's lungs for a given amount of delivered pressure. Lower resistance may necessitate, inter alia, a lower $P_I$ (or $P_{SUPP}$) setting or a shorter inspiratory time setting ($T_I$) for delivering a prescribed pressure or volume of gases (resulting in a higher expiratory time, $T_E$), to allow for complete exhalation of gases, etc. Indeed, if the delivered $V_T$ exceeds some threshold value (e.g., a threshold $V_T$ setting), the ventilator may detect high-delivered $V_T$. In some cases, the ventilator may detect high-delivered $V_T$, but may not issue an alarm when the high-delivered $V_T$ is within acceptable ranges. In this case, the clinician may be unaware that high-delivered $V_T$ was detected unless the ventilator issues a suitable notification (e.g., a smart prompt).

Pressure Data

According to embodiments, data processing module 222 may be configured to monitor pressure. Pressure may be measured by any appropriate, internal or distributed device or sensor within the ventilatory system. For example, pressure may be monitored by proximal electromechanical transducers connected near the airway opening (e.g., on the inspiratory limb, expiratory limb, at the patient interface, etc.). Alternatively, pressure may be monitored distally, at or near the lungs and/or diaphragm of the patient.

For example $P_{Peak}$ and/or $P_{Plat}$ (estimating $P_a$) may be measured proximally (e.g., at or near the airway opening) via single-point pressure measurements. According to embodiments, $P_{Plat}$ (estimating $P_a$) may be measured during an inspiratory pause maneuver (e.g., exhalation and inhalation valves are closed briefly at the end of inspiration for measuring the $P_{Plat}$ at zero flow). According to other embodiments, circuit pressure may be measured during an expiratory pause maneuver (e.g., exhalation and inhalation valves are closed briefly at the end of exhalation for measuring EEP at zero flow). Alternatively, $P_m$ may be distally measured (e.g., at or near the lungs and/or diaphragm) via multiple-point pressure measurements. Upon collecting $P_m$ data, the ventilator may conduct calculations to quantify patient effort, which may be further used to estimate the patient's resistance and compliance. According to some embodiments, spontaneously-breathing patients may need to be sedated before taking some of the above-described pressure measurements.

Data processing module 222 may be further configured to plot monitored pressure data graphically via any suitable means. For example, according to embodiments, pressure data may be plotted versus time (pressure waveform), versus volume (pressure-volume loop or PV loop), or versus any other suitable parameter as may be useful to a clinician. According to embodiments, pressure may be plotted such that each breath may be independently identified. Further, pressure may be plotted such that inspiratory pressure and expiratory pressure may be independently identified, e.g., inspiratory pressure may be represented in one color and expiratory pressure may be represented in another color. According to additional embodiments, pressure waveforms and PV loops, for example, may be represented alongside additional graphical representations, e.g., representations of volume, flow, etc., such that a clinician may substantially simultaneously visualize a variety of parameters associated with each breath.

According to embodiments, PV loops may provide useful clinical and diagnostic information to clinicians regarding the resistance and/or compliance of a patient. Specifically, upon comparing PV loops from successive breaths, a change in resistance over time may be detected. For example, at constant pressure when resistance is decreasing, more volume is delivered to the lungs resulting in a longer, narrower PV loop. Alternatively, at constant pressure when resistance is increasing, less volume is delivered to the lungs resulting in a shorter, wider PV loop. According to alternative embodiments, a PV loop may provide a visual representation indicative of compliance, that is, the area between the inspiratory plot of pressure vs. volume and the expiratory plot of pressure vs. volume. Thus, PV loops may also be compared to one another to determine whether compliance has changed over time.

According to additional embodiments, PV curves may be used to compare $C_S$ and $C_D$ over a number of breaths. For example, a first PV curve may be plotted for $C_S$ (based on $P_{Plat}$ less EEP) and a second PV curve may be plotted for $C_D$ (based on $P_{Peak}$ less EEP). Under normal conditions, $C_S$ and $C_D$ curves may be very similar, with the $C_D$ curve mimicking the $C_S$ curve but shifted to the right (i.e., plotted at higher pressure). However, in some cases the $C_D$ curve may flatten out and shift to the right relative to the $C_S$ curve. This graphical representation may illustrate increasing $P_t$, and thus increasing R, which may be due to mucous plugging or bronchospasm, for example. In other cases, both the $C_D$ curve and the $C_S$ curves may flatten out and shift to the right. This graphical representation may illustrate an increase in $P_{Peak}$ and $P_{Plat}$, without an increase in $P_t$, and thus may implicate a decrease in lung compliance, which may be due to tension pneumothorax, atelectasis, pulmonary edema, pneumonia, bronchial intubation, etc.

As may be further appreciated, relationships between resistance, static compliance, dynamic compliance, and various pressure readings may give indications of patient condition. For example, when $C_S$ increases, $C_D$ increases and, similarly, when R increases, $C_D$ increases. Additionally, as discussed previously, $P_t$ represents the difference in pressure attributable to resistive forces over elastic forces. Thus, where $P_{Peak}$ and $P_t$ are increasing with constant $V_T$ delivery, R is increasing (i.e., where $P_{Peak}$ is increasing without a concomitant increase in $P_{Plat}$). Where $P_t$ is roughly constant, but where $P_{Peak}$ and $P_{Plat}$ are increasing with a constant $V_T$ delivery, $C_S$ is increasing.

Volume Data

According to embodiments, data processing module 222 may be configured to derive volume via any suitable means. For example, as described above, during volume ventilation, a prescribed $V_T$ may be set for delivery to the patient. In some cases, as a result of patient effort, the patient may "out-draw" the set $V_T$, resulting in a higher delivered $V_T$ than the set $V_T$. Thus, for either volume or pressure ventilation, delivered $V_T$ may be determined at the end of inspiration, i.e., by integrating net inspiratory flow over $T_I$ (either set $T_I$ or patient-determined $T_I$). Alternatively, expiratory flow may be monitored such that exhaled tidal volume ($V_{TE}$) may be derived by integrating net expiratory flow over expiratory time ($T_E$). In general, the delivered $V_T$ should be completely exhaled and, thus, $V_{TE}$ should be equivalent to delivered $V_T$. Indeed, delivered $V_T$ may be determined via any suitable means, either currently known or developed in the future.

Data processing module 222 may be further configured to plot the volume data graphically via any suitable means. For example, according to embodiments, volume data may be plotted versus time (volume waveform), versus flow (flow-volume loop or FV loop), or versus any other suitable parameter as may be useful to a clinician. According to embodiments, volume may be plotted such that each breath may be independently identified. Further, volume may be plotted such that delivered $V_T$ and $V_{TE}$ may be independently identified, e.g., delivered $V_T$ may be represented in one color and $V_{TE}$ may be represented in another color. According to additional embodiments, volume waveforms and FV loops, for example, may be represented alongside additional graphical representations, e.g., representations of pressure, flow, etc., such that a clinician may substantially simultaneously visualize a variety of parameters associated with each breath.

High-Delivered $V_T$

Ventilator 202 may further include a high-delivered $V_T$ detection module 224. As described above, delivered $V_T$ may be determined via any suitable means. Thereafter, delivered $V_T$ may be compared to a threshold $V_T$ setting. The threshold $V_T$ may be prescribed by a physician or dictated by any suitable institutional or other protocol. According to some embodiments, the clinician may not input the threshold $V_T$ setting, but it may be automatically generated by the ventilator based on attributes of the patient (e.g., age, gender, diagnosis, PBW or IBW, etc.) or based on a default value. According to some embodiments, the threshold $V_T$ setting may be selectable by a clinician between 5 and 15 ml/kg, with an automatic default value of 7 ml/kg. According to alternative embodiments, the selectable range for the threshold $V_T$ setting may be any suitable range (e.g., between 3 and 20 ml/kg, between 10 and 25 ml/kg, etc.) and the default value may be any suitable value (e.g., 5 ml/kg, 8 ml/kg, 10 ml/kg, etc.).

According to embodiments, when the delivered $V_T$ is greater than the threshold $V_T$, the ventilator may detect high-delivered $V_T$. According to alternative embodiments, high-delivered $V_T$ may be detected when delivered $V_T$ is greater than the threshold $V_T$ for a threshold time period (e.g., delivered $V_T$ is greater than the threshold $V_T$ for 2 consecutive breaths, for 3 of 5 consecutive breaths, for 30% of breaths over a period of time, etc.). In some cases, high-delivered $V_T$ may be dangerous to the patient. For instance, when too much volume is delivered to a patient's lungs, the lungs may become over-distended, causing barotraumas or other damage to the lungs. Additionally, over-distension of the lungs has been linked to higher mortality rates in ventilated patients. Alternatively, when too much volume is delivered to the lungs, the expiratory time ($T_E$) may be insufficient to completely exhale the delivered volume, potentially resulting in Auto-PEEP (i.e., gas trapping in the lungs that may also lead to barotraumas and an increase the patient's work of breathing, WOB). In other cases, high-delivered $V_T$ may be indicative of improving patient condition (e.g., increased compliance and/or decreased resistance). In still other cases, high-delivered $V_T$ may be the result of increased inspiratory effort by the patient, suggesting that the patient desires more volume than provided by the current $V_T$ setting. Indeed, this issue may be compounded when the ventilator is delivering VC+ or VS breath types. That is, if the patient exhibits inspiratory effort resulting in high-delivered $V_T$, in the next breath the ventilator will adjust the effective pressure downward to achieve the set $V_T$, providing even less volume to the patient. In response, the patient may exhibit more inspiratory effort to draw in the desired volume and the ventilator may respond by again adjusting effective pressure downward to achieve the set $V_T$. Indeed the patient may continue to "fight" the ventilator until the ventilator reaches a minimum effective pressure and alarms. This process may be exhausting to the patient and may ultimately result in insufficient ventilation.

Due to the variety of potential causes for high-delivered $V_T$, the high-delivered $V_T$ detection module 224 may further comprise a potential cause detection module 226. That is, the potential cause detection module 226 may evaluate various ventilatory data to determine potential causes for the high-delivered $V_T$. For example, the potential cause detection module 226 may determine whether the high-delivered $V_T$ occurred concurrently with a decrease in resistance, an increase in compliance, an increase in patient inspiratory effort, etc.

That is, according to embodiments, potential cause detection module 226 may evaluate various ventilatory data to determine whether resistance is decreasing. Resistance may decrease for a number of reasons, including changing lung conditions (e.g., bronchial relaxation after medication, reduced infection and/or fluid, etc.), improved body position, a leak in the ventilatory circuit, etc. For example, the potential cause detection module 226 may trend resistance values for the patient via any suitable means. "Trending," as used herein, means collecting and/or deriving data over a plurality of breaths (or at predetermined intervals of time). For example, according to embodiments, the potential cause detection module 226 may trend resistance by evaluating a plurality of successive PV loops. According to alternative embodiments, the potential cause detection module 226 may trend resistance by trending flow data at a constant pressure (e.g., over a number of breaths during pressure-based ventilation, during successive maneuvers, etc.). In this case, where other variables are known and/or constant, if flow is increasing over time at constant pressure, resistance is decreasing, whereas if flow is decreasing over time at constant pressure, resistance is increasing (i.e., $R=P_t/F$). According to alternative embodiments, potential cause detection module 226 may calculate and trend resistance based on any suitable mathematical equation or formula (e.g., $R=P_t/F$). According to other embodiments, resistance may be determined and trended via any suitable means.

The trended resistance data may be compared to, for example, a resistance threshold to detect a decrease in resistance. The resistance threshold may refer to a percentage reduction in resistance (e.g., decrease of 10%, 20%, 25%, 30%, or any other suitable percentage). Alternatively, the resistance threshold may refer to a value reduction in resistance (e.g., reduction of 2 cmH$_2$O/L/s, 3 cmH$_2$O/L/s, 5 cmH$_2$O/L/s, or any other suitable value). Indeed, according to embodiments, the resistance threshold may be established according to any appropriate criteria (e.g., an appropriate standard, protocol, or otherwise) and may be configured by a manufacturer, an institution, a clinician, or otherwise. When the trended resistance data breaches the resistance threshold, the potential cause detection module 226 may detect a decrease in resistance. Further, if the decrease in resistance was detected concurrently with the high-delivered V$_T$ (e.g., during the previous 2 hours or since the start of ventilation, whichever is less), the potential cause detection module 226 may determine that the decrease in resistance was a potential cause for the high-delivered V$_T$.

According to alternative embodiments, potential cause detection module 226 may evaluate various ventilatory data to determine whether compliance is increasing. That is, when elastance decreases (e.g., forces opposing lung inflation), it may require less pressure to deliver a particular volume (i.e., $\Delta V = C^* \Delta P$). Consequently, additional volume may be delivered at constant pressure and may over-distend the lungs and/or result in gas-trapping. For example, potential cause detection module 226 may calculate and trend compliance based on any suitable mathematical equation or formula (e.g., $\Delta V = C^* \Delta P$). According to alternative embodiments, potential cause detection module 226 may evaluate PV loops based on one or more predetermined thresholds to detect whether compliance is increasing, i.e., by comparing the area between the inspiratory plot of pressure versus volume and the expiratory plot of pressure versus volume over a number of breaths. According to alternative embodiments, potential cause detection module 226 may evaluate PV curves to compare C$_S$ and C$_D$ over a number of breaths. That is, where both the C$_D$ curve and the C$_S$ curve straighten and shift to the left (e.g., illustrating decreasing P$_{Peak}$ and P$_{Plat}$) compliance may be increasing. According to other embodiments, compliance may be determined and trended via any suitable means.

Trended compliance data may be compared to, for example, a compliance threshold to detect an increase in compliance. The compliance threshold may refer to a percentage increase in compliance (e.g., increase of 10%, 20%, 25%, 30%, or any other suitable percentage increase). Alternatively, the compliance threshold may refer to a value increase in compliance (e.g., increase of 5 mL/cmH$_2$O, 10 mL/cmH$_2$O, or any other suitable value increase). Indeed, according to embodiments, the compliance threshold may be established according to any appropriate criteria (e.g., an appropriate standard, protocol, or otherwise) and may be configured by a manufacturer, an institution, a clinician, or otherwise. When the trended compliance data breaches the compliance threshold, the potential cause detection module 226 may detect an increase in compliance. Further, if the increase in compliance was detected concurrently with the high-delivered V$_T$ (e.g., during the previous 2 hours or since the start of ventilation, whichever is less), the potential cause detection module 226 may determine that the increase in compliance was a potential cause for the high-delivered V$_T$.

According to alternative embodiments, potential cause detection module 226 may evaluate various ventilatory data to determine whether patient inspiratory effort has increased. If patient inspiratory effort has increased, the patient may draw additional volume into the lungs. As described above, P$_m$ may be measured or derived by the ventilator and thereafter manipulated to quantify or estimate patient effort (e.g., yielding patient effort data in cmH$_2$O, cmH$_2$O/s, or J/L). Alternatively, the ventilator may be configured to conduct a maneuver (e.g., P$_{100}$ maneuver) at the beginning of inspiration to detect patient effort. For example, the ventilator may delay delivering gases for a short period of time at the beginning of inspiration (e.g., about 100 ms) and may measure the pressure generated by the patient due to inspiratory effort. The resulting pressure data, P$_{100}$ data, may also represent an estimate of patient effort (e.g., yielding patient effort data in cmH$_2$O). The P$_{100}$ data may be compared to a pre-configured range of pressure values that correspond to different levels of patient effort. For example, pressures between 0.0-0.5 cmH$_2$O may be indicative of low or no patient effort, pressures between 2-3 cmH$_2$O may be indicative of normal patient effort, and pressures 6-7 cmH$_2$O may be indicative of high patient effort (i.e., "pulling").

According to embodiments, the ventilator may detect whether patient inspiratory effort has increased by comparing patient effort data (e.g., based on P$_m$ data, P$_{100}$ data, or otherwise) to an effort threshold. When comparing patient effort data based on P$_m$ data to the effort threshold, depending on the unit of measurement for the patient effort data (e.g., cmH$_2$O, cmH$_2$O/s, EL, etc.), the effort threshold may be represented in the same unit of measurement. When comparing patient effort data based on P$_{100}$ data to the effort threshold, the effort threshold may be represented in units of pressure (e.g., cmH$_2$O). According to embodiments, the effort threshold may refer to a percentage increase in effort generated by the patient (e.g., an increase of 10%, 20%, 25%, 30%, or any other suitable percentage increase). Alternatively, the effort threshold may refer to a value increase in effort generated by the patient (e.g., an increase of 1 cmH$_2$O, 2 cmH$_2$O, an increase of 1 cmH$_2$O/s, 2 cmH$_2$O/s, etc., or other suitable increase). Indeed, the ventilator may determine whether patient inspiratory effort has increased via any suitable method either currently known or developed in the future. When the patient effort data breaches the effort threshold, the potential cause detection module 226 may detect an increase in patient inspiratory effort. Further, if the increase in patient inspiratory effort was detected concurrently with the high-delivered V$_T$ (e.g., during the previous 2 hours or since the start of ventilation, whichever is less), the potential cause detection module 226 may determine that the increase in patient inspiratory effort was a potential cause for the high-delivered V$_T$.

Smart-Prompt Generation

Ventilator 202 may further include a smart prompt module 228. As described above, the occurrence of and potential causes for high-delivered V$_T$ may be very difficult for a clinician to detect. As may be appreciated, multiple ventilatory parameters may be monitored and evaluated in order to detect an occurrence of and potential causes for high-delivered V$_T$. As such, upon detection of high-delivered V$_T$, the smart prompt module 228 may be configured to notify the clinician that high-delivered V$_T$ has occurred and/or to provide one or more potential causes for the high-delivered V$_T$. Furthermore, the ventilator may provide one or more suggestions or recommendations for addressing the high-delivered V$_T$. For example, smart prompt module 228 may be configured to notify the clinician by displaying a smart prompt on display monitor 204 and/or within a window of the GUI. According to additional embodiments, the smart prompt may be communicated to and/or displayed on a remote monitoring system communicatively coupled to ventilatory system 200. Alternatively, in an automated embodiment, the smart prompt module 228 may communicate with a ventilator control system so that the one or more recommendations may be automatically implemented to address the high-delivered V$_T$.

In order to accomplish the various aspects of the notification and/or recommendation message display, the smart prompt module 228 may communicate with various other components and/or modules. For instance, smart prompt module 228 may be in communication with data processing module 222, high-delivered $V_T$ detection module 224, potential cause detection module 226, or any other suitable module or component of the ventilatory system 200. That is, smart prompt module 228 may receive an indication that high-delivered $V_T$ has been detected by any suitable means. In addition, smart prompt module 228 may receive information regarding one or more potential causes for the high-delivered $V_T$. Further still, smart prompt module 228 may determine and offer one or more recommendations for addressing the high-delivered $V_T$.

Smart prompt module 228 may further comprise additional modules for making notifications and/or recommendations to a clinician regarding the occurrence of high-delivered $V_T$. For example, according to embodiments, smart prompt module 228 may include a notification module 230 and a recommendation module 232. For instance, smart prompts may be provided according to a hierarchical structure such that a notification message and/or a recommendation message may be initially presented in summarized form and, upon clinician selection, an additional detailed notification and/or recommendation message may be displayed. According to alternative embodiments, a notification message may be initially presented and, upon clinician selection, a recommendation message may be displayed. Alternatively or additionally, the notification message may be simultaneously displayed with the recommendation message in any suitable format or configuration.

Specifically, according to embodiments, the notification message may alert the clinician as to the detection of a patient condition, a change in patient condition, or an effectiveness of ventilatory treatment. For example, the notification message may alert the clinician that high-delivered $V_T$ has been detected. The notification message may further alert the clinician regarding potential causes for the high-delivered $V_T$ (e.g., high-delivered $V_T$ detected concurrent with an increase in dynamic lung/chest wall compliance, high-delivered $V_T$ detected concurrent with a decrease in resistance, high-delivered $V_T$ detected concurrent with an increase in patient inspiratory effort, etc.)

Additionally, according to embodiments, the recommendation message may provide various suggestions to the clinician for addressing a detected condition. The recommendation message may further be specific to a particular type of ventilation. Far example, high-delivered $V_T$ may be detected concurrent with an increase in dynamic compliance (or a decrease in resistance). In this case, if the ventilator is delivering PC ventilation, the ventilator may provide the recommendation: "Consider reducing set $P_I$." Alternatively, if the ventilator is delivering PS ventilation, the ventilator may provide the recommendation: "Consider reducing set $P_{SUPP}$."

According to alternative embodiments, the high-delivered $V_T$ may be detected concurrent with an increase in patient inspiratory effort. In this case, if the ventilator is delivering PC ventilation, the ventilator may provide the recommendation: "Consider: (1) causes for increased patient inspiratory effort; (2) reducing set $P_I$." Alternatively, if the ventilator is delivering PS ventilation, the ventilator may provide the recommendation: "Consider: (1) causes for increased patient inspiratory effort; (2) reducing set $P_{SUPP}$." Alternatively, if the ventilator is delivering VC, VC+ or VS ventilation, the ventilator may provide the recommendation: "Consider: (1) causes for increased patient inspiratory effort; (2) increasing set $V_T$." Alternatively still, if the ventilator is delivering PA ventilation, the ventilator may provide the recommendation: "Consider causes for increased patient inspiratory effort."

As described above, smart prompt module 228 may also be configured with notification module 230 and recommendation module 232. The notification module 230 may be in communication with data processing module 222, high-delivered $V_T$ detection module 224, potential cause detection module 226, or any other suitable module or component to receive an indication that high-delivered $V_T$ has been detected and identification of one or more potential causes for the high-delivered $V_T$. Notification module 230 may be responsible for generating a notification message via any suitable means. For example, the notification message may be provided as a tab, banner, dialog box, or other similar type of display. Further, the notification message may be provided along a border of the graphical user interface, near an alarm display or bar, or in any other suitable location. A shape and size of the notification message may further be optimized for easy viewing with minimal interference to other ventilatory displays. The notification message may be further configured with a combination of icons and text such that the clinician may readily identify the message as a notification message. The notification message may further be associated with a primary prompt.

The recommendation module 232 may be responsible for generating one or more recommendation messages via any suitable means. The one or more recommendation messages may provide suggestions and information regarding addressing a detected condition and may be accessible from the notification message. For example, the one or more recommendation messages may provide suggestions for adjusting one or more ventilatory parameters to address the detected condition, may provide suggestions for checking ventilatory equipment or the patient, or may provide other helpful information. Specifically, the one or more recommendation messages may provide suggestions and information regarding addressing high-delivered $V_T$. The one or more recommendation messages may further be associated with a secondary prompt.

As noted above, according to embodiments, the notification message may be associated with a primary prompt and the one or more recommendation messages may be associated with a secondary prompt. That is, a primary prompt may provide an alert that high-delivered $V_T$ has been detected and may further provide one or more potential causes for the high-delivered $V_T$. Alternatively, an alert may be separately provided, indicating that high-delivered $V_T$ was detected, and the primary prompt may provide the one or more potential causes for the high-delivered $V_T$. According to additional or alternative embodiments, the secondary prompt may provide the one or more recommendations and/or information that may aid the clinician in further addressing and/or mitigating the detected condition. For example, the secondary prompt may recommend addressing the high-delivered $V_T$ by reducing set $P_I$ (or set $P_{SUPP}$), by investigating causes for increased inspiratory effort, by increasing the set $V_T$, etc. According to further embodiments, a single smart prompt may be displayed (i.e., not configured with a primary prompt and a secondary prompt) and may include at least one of: a notification that high-delivered $V_T$ occurred, one or more potential causes for the high-delivered $V_T$, and/or one or more recommendations for addressing the high-delivered $V_T$. According to alternative embodiments, the secondary prompt described above may be provided as the primary prompt and the primary prompt described above may be provided as the secondary prompt.

Smart prompt module 228 may also be configured such that smart prompts (including alerts, primary prompts, and/or secondary prompts) may be displayed in a partially transparent window or format. The transparency may allow for notification and/or recommendation messages to be displayed such that normal ventilator GUI and ventilatory data may be visualized behind the messages. As described previously, notification and/or recommendation messages may be displayed in areas of the display screen that are either blank or that cause minimal distraction from the ventilatory data and other graphical representations provided by the GUI. However, upon selective expansion of a smart prompt, ventilatory data and graphs may be at least partially obscured. As a result, translucent display may provide the smart prompt such that it is partially transparent. Thus, graphical and other data may be visible behind the smart prompt.

Additionally, alerts, primary prompts, and/or secondary prompts may provide immediate access to the display and/or settings screens associated with the detected condition. For example, an associated parameter settings screen may be accessed from a smart prompt via a hyperlink such that the clinician may address the detected condition as necessary. An associated parameter display screen may also be accessed such that the clinician may view clinical data associated with the detected condition in the form of charts, graphs, or otherwise. For example, when high-delivered $V_T$ has been detected, depending on the one or more potential causes for the high-delivered $V_T$, the clinician may be able to access ventilatory settings for addressing high-delivered $V_T$ (e.g., a settings screen for adjusting set $P_I$, set $P_{SUPP}$, set $V_T$, etc.) and/or to view ventilatory data associated with the one or more potential causes for the high-delivered $V_T$ (e.g., charts displaying historical data and/or graphics displaying historical flow waveforms, volume waveforms, and/or pressure waveforms that implicated decreased resistance, increased compliance, increased inspiratory effort, etc.).

According to embodiments, upon viewing a smart prompt (including any associated alert, primary prompt, and/or secondary prompt), upon addressing the detected condition by adjusting one or more ventilatory settings or otherwise, or upon manual selection, the smart prompt may be cleared from the GUI. For example, according to some embodiments, upon receiving a ventilatory settings change, the ventilator may reset detection of high-delivered $V_T$ when two consecutive breaths exhibit delivered $V_T$ less than the $V_T$ threshold setting or when all breaths over the previous 30 seconds exhibit delivered $V_T$ less than the $V_T$ threshold setting. According to alternative embodiments, in the absence of user activity, the ventilator may reset detection of high-delivered $V_T$ when all breaths over the previous 60 seconds exhibit delivered $V_T$ less than the $V_T$ threshold setting. Thereafter, upon resetting detection of high-delivered $V_T$, the ventilator may clear the smart prompt from the GUI and resume evaluation of ventilatory data by the high-delivered $V_T$ detection module 224 and the potential cause detection module 226.

High-Delivered $V_T$ Detection and Notification

Figure 3:
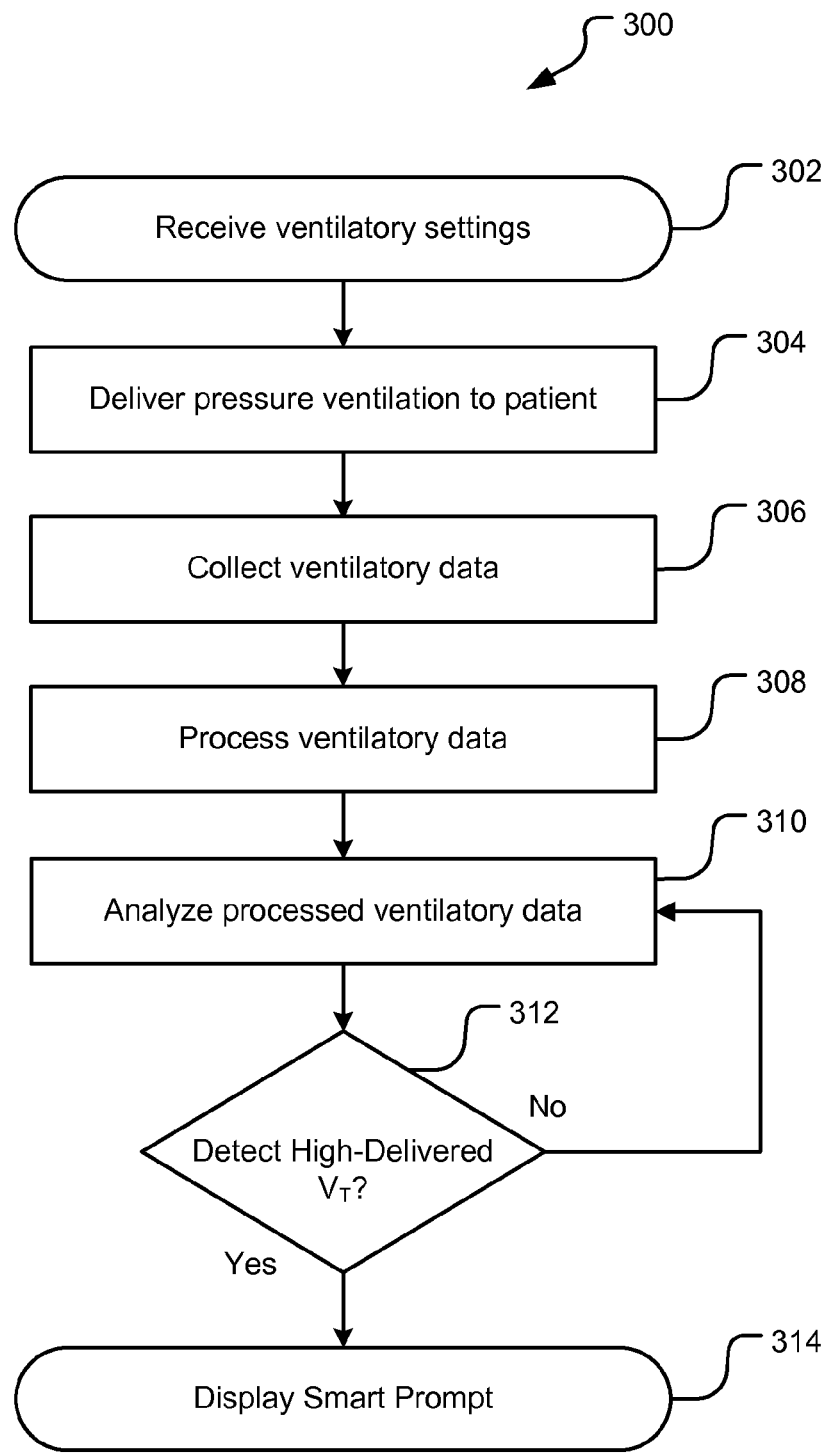
FIG. 3 is a flow chart illustrating an embodiment of a method for detecting high-delivered $V_T$ and issuing a suitable smart prompt.

FIG. 3 is a flow chart illustrating an embodiment of a method for detecting high-delivered $V_T$ and issuing a suitable smart prompt.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

The illustrated embodiment of the method 300 depicts a method for detecting high-delivered $V_T$. According to embodiments described herein, ventilation delivered may generally include volume control (VC) ventilation, pressure control (PC) ventilation, pressure support (PS) ventilation, volume-targeted-pressure-control (VC+), volume-targeted-pressure-support (VS), proportional assist (PA) ventilation, etc.

Method 300 begins with a receive settings operation 302. For example, at receive settings operation 302, the ventilator may receive one or more ventilatory settings associated with a type of ventilation (e.g., VC, PC, PS, VC+, VS, or PA ventilation). For example, according to embodiments, the ventilator may be configured to provide VC ventilation to a patient. As such, the ventilatory settings may include a set $V_T$, a respiratory rate (RR), an inspiratory time ($T_I$), a patient PBW or IBW, PEEP, a threshold $V_T$, etc. For example, according to alternative embodiments, the ventilator may be configured to provide PC ventilation to a patient. As such, the ventilatory settings may include an inspiratory pressure ($P_I$), a respiratory rate (RR), an inspiratory time ($T_I$), a patient PBW or IBW, PEEP, a threshold $V_T$, rise time %, etc. According to alternative embodiments, the ventilator may be configured to provide PS ventilation to a patient. As such, the ventilatory settings and/or input received may include a pressure support setting ($P_{SUPP}$), a patient PBW or IBW, PEEP, a threshold $V_T$ setting, a rise time %, etc. According to alternative embodiments, the ventilator may be configured to provide VC+ ventilation to a patient. As such, the ventilatory settings may include an inspiratory pressure ($P_I$), a respiratory rate (RR), an inspiratory time ($T_I$), a set (or target) $V_T$, a patient PBW or IBW, PEEP, a threshold $V_T$, rise time %, etc. According to alternative embodiments, the ventilator may be configured to provide VS ventilation to a patient. As such, the ventilatory settings may include a pressure support setting ($P_{SUPP}$), a set (or target) $V_T$, a patient PBW or IBW, a threshold $V_T$, rise time %, etc. According to still alternative embodiments, the ventilator may be configured to provide PA ventilation to a patient. As such, the ventilatory settings may include a percent support setting, a patient PBW or IBW, PEEP, a threshold $V_T$, tube type and internal diameter (I.D.), etc.

According to some embodiments, the clinician may select one or more of the ventilatory settings from a range of options. Alternatively, one or more of the ventilatory settings may be automatically generated by the ventilator based on a default value or based on one or more attributes of the patient (e.g., age, gender, diagnosis, PBW or IBW, etc.). For example, according to some embodiments, the threshold $V_T$ setting may be selectable by a clinician between 5 and 15 ml/kg, with an automatic default value of 7 ml/kg. According to alternative embodiments, the selectable range for the threshold $V_T$ setting may be any suitable range (e.g., between 3 and 20 ml/kg, between 10 and 25 ml/kg, etc.) and the default value may be any suitable value (e.g., 5 ml/kg, 8 ml/kg, 10 ml/kg, etc.). Alternatively still, the threshold $V_T$ setting may be automatically generated by the ventilator based on one or more patient attributes or otherwise.

At deliver ventilation operation 304, the ventilator provides ventilation to the patient, as described above. That is, according to embodiments, the ventilator may deliver VC, PC, PS, VC+, VS, or PA breath types to a patient. According to additional embodiments, the ventilator may deliver breath types to the patient according to various ventilatory modes (e.g., A/C, spontaneous, BiLevel, SIMV, etc.). For example, during VC ventilation, the ventilator may deliver a set peak flow and flow pattern for a period of time, i.e., set inspiratory time ($T_I$). Based on the set peak flow, flow pattern and patient inspiratory effort (if any), a volume of gases will be delivered to the patient's lungs (i.e., delivered $V_T$). For example, during PC or VC+ ventilation, the ventilator may deliver an effective pressure (equivalent to PEEP plus set $P_I$) at the patient airway for a period of time, i.e., set inspiratory time ($T_I$). Based on the effective pressure, resistance, compliance and patient inspiratory effort (if any), a volume of gases will be delivered to the patient's lungs (i.e., delivered $V_T$). Alternatively, during PS or VS ventilation, the ventilator may deliver an effective pressure (equivalent to PEEP plus set $P_{SUPP}$) at the patient airway. Based on the effective pressure, resistance, compliance and patient inspiratory effort, a volume of gases will be delivered to the patient's lungs (i.e., delivered $V_T$). Alternatively still, during PA ventilation, the ventilator may target a pressure at the patient airway that is a function of the percent support, PEEP, an estimate of the patient's resistance and elastance, and a calculation of the tube resistance. Based on the target pressure, resistance, compliance, and patient inspiratory effort, a volume of gases will be delivered to the patient's lungs (i.e., delivered $V_T$). Furthermore, the ventilator may initiate an exhalation phase when a set $T_I$ has been reached, when patient exhalation cycling is detected, or based on any other appropriate cycling criterion.

At collect ventilatory data operation 306, the ventilator may collect various ventilatory data associated with ventilation of a patient. For example, as described above, the ventilator may collect ventilatory data regarding flow and pressure parameters. The ventilator may collect the ventilatory data via any suitable means, e.g., any internal or distributed sensor including flowmeters, pressure transducers, etc.

At process ventilatory data operation 308, the ventilator may conduct various data processing operations. For example, at data processing operation 308, the ventilator may derive various ventilatory data associated with the ventilation of a patient. For example, as described above, the ventilator may collect ventilatory data regarding flow and pressure parameters. Additionally, the ventilator may derive ventilatory data based on the collected data, e.g., delivered volume, resistance, compliance, patient effort, etc. For example, delivered volume (delivered $V_T$) may be determined based on integrating the net flow during the last inspiration and applying various volume compensations (e.g., tube compliance). Additionally, the ventilator may generate various graphical representations of the collected and/or derived ventilatory data, e.g., including charts, graphs depicting flow waveforms, pressure waveforms, pressure-volume loops, flow-volume loops, or other suitable data representations.

At analyze operation 310, the ventilator may evaluate the processed ventilatory data to determine whether a certain patient condition exists. For example, according to embodiments, the ventilator may analyze the delivered $V_T$ in light of a threshold $V_T$ setting. As described above, the threshold $V_T$ may be received as input from the clinician or may be automatically generated by the ventilator based on a default value or based on the patient's PBW or other appropriate criteria (e.g., based on a suitable protocol or otherwise). According to embodiments, the ventilator may analyze the ventilatory data by comparing the delivered $V_T$ to the threshold $V_T$ via any suitable means.

At detect high-delivered $V_T$ operation 312, the ventilator may determine whether high-delivered $V_T$ occurred. For example, upon comparing the delivered $V_T$ to the threshold $V_T$ in the analyze operation above, the ventilator may determine that delivered $V_T$ is greater than the threshold $V_T$ and the ventilator may detect high-delivered $V_T$. Alternatively, according to some embodiments, the ventilator may determine that high-delivered $V_T$ occurred when delivered $V_T$ is greater than the threshold $V_T$ over a threshold time period (e.g., delivered $V_T$ is greater than the threshold $V_T$ for 2 consecutive breaths, for 3 of 5 consecutive breaths, for 30% of breaths over a period of time, etc.). If high-delivered $V_T$ is detected, the operation may proceed to display smart prompt operation 314. If high-delivered $V_T$ is not detected, the operation may return to analyze operation 310.

At display smart prompt operation 314, the ventilator may alert the clinician via any suitable means that high-delivered $V_T$ was detected. For example, according to embodiments, the ventilator may display a smart prompt including a notification message and/or one or more recommendation messages regarding the detection of high-delivered $V_T$ on the GUI. According to alternative embodiments, the ventilator may communicate the smart prompt, including the notification message and/or the one or more recommendation messages, to a remote monitoring system communicatively coupled to the ventilator. According to some embodiments, the high-delivered $V_T$ may fall within acceptable predetermined ranges such that the ventilator does not issue an alarm upon detecting the high-delivered $V_T$. That is, the high-delivered $V_T$ may be detected for purposes of generating a smart prompt, but may not rise to the level of alarm generation.

Figure 4:
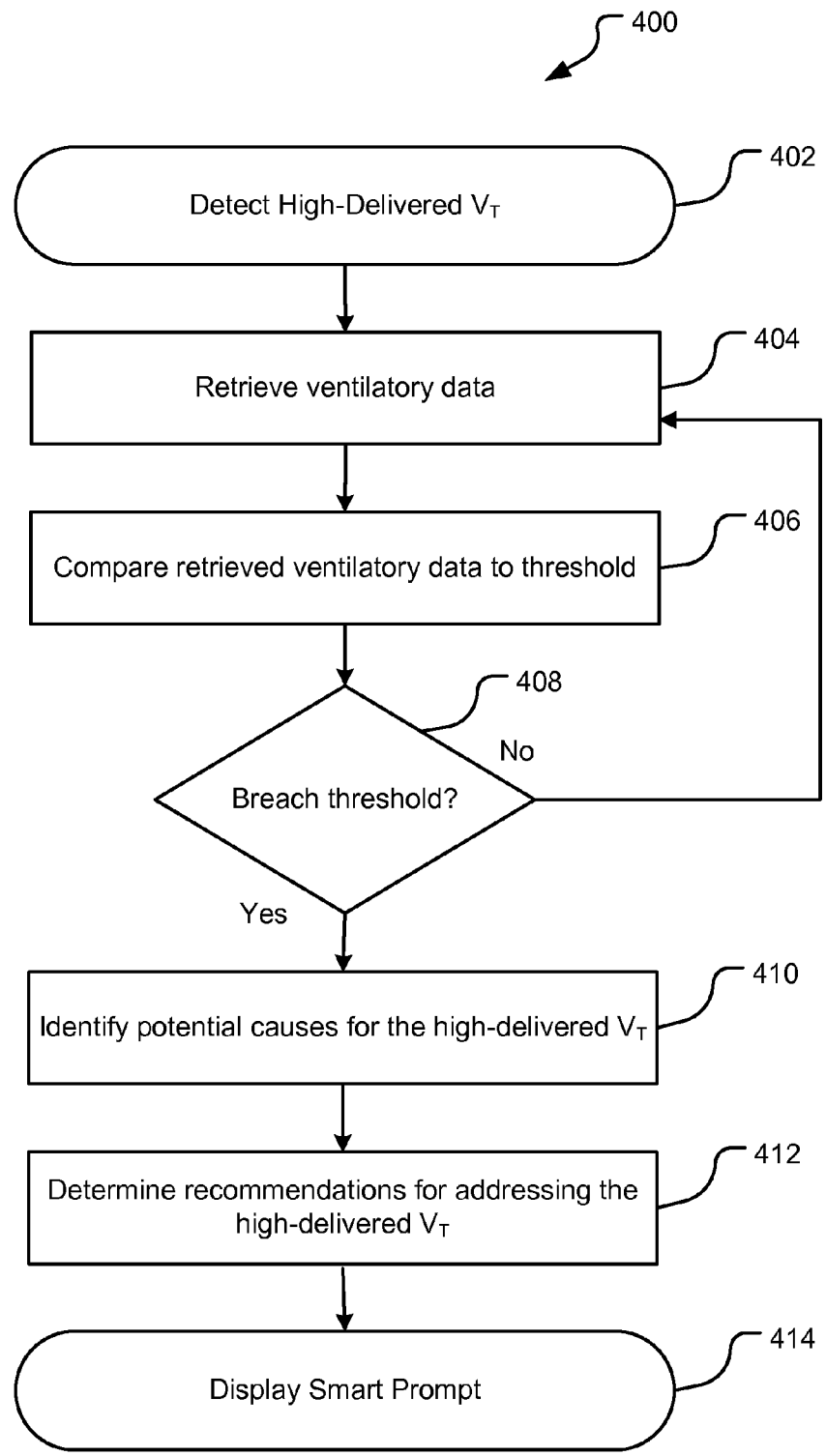
FIG. 4 is a flow chart illustrating an embodiment of a method for detecting potential causes for high-delivered $V_T$ and issuing a suitable smart prompt.

FIG. 4 is a flow chart illustrating an embodiment of a method for detecting potential causes for high-delivered $V_T$ and issuing a suitable smart prompt.

As should be appreciated, the particular steps and methods described herein are not exclusive and, as will be understood by those skilled in the art, the particular ordering of steps as described herein is not intended to limit the method, e.g., steps may be performed in differing order, additional steps may be performed, and disclosed steps may be excluded without departing from the spirit of the present methods.

The illustrated embodiment of the method 400 depicts a method for issuing a smart prompt upon detecting high-delivered $V_T$. Method 400 begins with detect operation 402, wherein the ventilator detects that high-delivered $V_T$ occurred, as described above in method 300.

At retrieve ventilatory data operation 404, the ventilator may retrieve various ventilatory data associated with, inter alia, resistance, compliance, and/or patient effort. For example, according to embodiments, the ventilator may retrieve resistance data generated based on evaluating a plurality of successive PV loops, based on evaluating flow data over time at constant pressure, or based on calculating resistance according to any suitable mathematical equation or formula. Additionally or alternatively, the ventilator may retrieve compliance data generated based on evaluating PV loops, PV curves, or based on calculating compliance according to any suitable mathematical equation or formula. Additionally or alternatively, the ventilator may retrieve patient effort data (e.g., based on $P_m$ data, $P_{100}$ data, or otherwise). Indeed, any other ventilatory data may be retrieved that may be indicative of other potential causes for high-delivered $V_T$.

At compare operation 406, the ventilator may compare the retrieved ventilatory data to a threshold. For example, retrieved resistance data may be compared to a resistance threshold to detect a decrease in resistance. The resistance threshold may refer to a percentage decrease in resistance (e.g., decrease of 10%, 20%, 25%, 30%, or any other suitable percentage decrease). Alternatively, the resistance threshold may refer to a value decrease in resistance (e.g., decrease of 2 $cmH_2O/L/s$, 3 $cmH_2O/L/s$, 5 $cmH_2O/L/s$, or any other suitable value decrease). Furthermore, the resistance threshold may involve a time component (e.g., decrease over a 2 hour period, from start of ventilation, or over a particular number of breaths). Indeed, according to embodiments, the resistance threshold may be established according to any appropriate criteria (e.g., an appropriate standard, protocol, or otherwise) and may be configured by a manufacturer, an institution, a clinician, or otherwise.

Additionally or alternatively, retrieved compliance data may be compared to, for example, a compliance threshold to detect an increase in compliance. The compliance threshold may refer to a percentage increase in compliance (e.g., increase of 10%, 20%, 25%, 30%, or any other suitable percentage). Alternatively, the compliance threshold may refer to a value increase in compliance (e.g., increase of 5 mL/cmH$_2$O, 10 mL/cmH$_2$O, or any other suitable value). Furthermore, the compliance threshold may involve a time component (e.g., increase over a 2 hour period, from start of ventilation, or over a particular number of breaths). Indeed, according to embodiments, the compliance threshold may be established according to any appropriate criteria (e.g., an appropriate standard, protocol, or otherwise) and may be configured by a manufacturer, an institution, a clinician, or otherwise.

Additionally or alternatively, retrieved patient effort data (e.g., based on $P_m$ data, $P_{100}$ data, or otherwise) may be compared to an effort threshold to detect an increase in patient inspiratory effort. The effort threshold may refer to a percentage increase in effort (e.g., increase of 10%, 20%, 25%, 30%, or any other suitable percentage). Alternatively, the effort threshold may refer to a value increase in effort (e.g., increase of 1 cmH$_2$O, 2 cmH$_2$O, or increase of 1 cmH$_2$O/s, 2 cmH$_2$O/s, or other suitable value). Furthermore, the effort threshold may involve a time component (e.g., increase over a 2 hour period, from start of ventilation, over a particular number of breaths, etc.). Indeed, according to embodiments, the effort threshold may be established according to any appropriate criteria (e.g., an appropriate standard, protocol, or otherwise) and may be configured by a manufacturer, an institution, a clinician, or otherwise.

At breach threshold determination operation 408, the ventilator may determine whether the compared ventilatory data breaches one or more thresholds. For example, when the resistance data breaches the resistance threshold, the ventilator may detect a decrease in resistance. Additionally or alternatively, when the compliance data breaches the compliance threshold, the ventilator may detect an increase in compliance. Additionally or alternatively, when the patient effort data (e.g., based on $P_m$ data, $P_{100}$ data, or otherwise) breaches the effort threshold, the ventilator may detect an increase in patient inspiratory effort. If the ventilator determined that the compared ventilatory data breached one or more thresholds, the operation may proceed to identify operation 410. If the ventilator determined that the compared ventilatory data did not breach one or more thresholds, the operation may return to retrieve ventilatory data operation 404.

At identify operation 410, the ventilator may determine one or more potential causes for the high-delivered $V_T$. For example, if the ventilator detected a decrease in resistance concurrently with the high-delivered $V_T$, the ventilator may determine that the decrease in resistance is a potential cause for the high-delivered $V_T$. That is, if the resistance data breached the resistance threshold over the previous 2 hours or since the start of ventilation (whichever is less), the ventilator may determine that the decrease in resistance was detected concurrently with the high-delivered $V_T$ and may identify the decrease in resistance as a potential cause for the high-delivered $V_T$. Alternatively, if the ventilator detected an increase in compliance concurrently with the high-delivered $V_T$, the ventilator may determine that the increase in compliance is a potential cause for the high-delivered $V_T$. That is, if the compliance data breached the compliance threshold over the previous 2 hours or since the start of ventilation (whichever is less), the ventilator may determine that the increase in compliance was detected concurrently with the high-delivered $V_T$ and may identify the increase in compliance as a potential cause for the high-delivered $V_T$. Alternatively still, if the ventilator detected an increase in patient effort concurrently with the high-delivered $V_T$, the ventilator may determine that the increase in patient effort is a potential cause for the high-delivered $V_T$. That is, if the patient effort data breached the effort threshold over the previous 2 hours or since the start of ventilation (whichever is less), the ventilator may determine that the increase in patient effort was detected concurrently with the high-delivered $V_T$ and may identify the increase in patient effort as a potential cause for the high-delivered $V_T$.

At determine operation 412, the ventilator may determine one or more recommendations for addressing the high-delivered $V_T$. The one or more recommendations may be based on a type of ventilation being delivered to the patient (e.g., VC, PC, PS, VC+, VS, or PA ventilation), based on a potential cause for the high-delivered $V_T$, or based on a combination thereof. For example, during PC ventilation, when high-delivered $V_T$ is detected concurrent with an increase in compliance or a decrease in resistance, the ventilator may provide the recommendation: "Consider reducing set $P_I$." Alternatively, when high-delivered $V_T$ is detected concurrent with an increase in patient inspiratory effort, the ventilator may provide the recommendation: "Consider: (1) causes for increased patient inspiratory effort; (2) reducing set $P_I$." During PS ventilation, when high-delivered $V_T$ is detected concurrent with an increase in compliance or a decrease in resistance, the ventilator may provide the recommendation: "Consider reducing set $P_{SUPP}$." Alternatively, when high-delivered $V_T$ is detected concurrent with an increase in patient inspiratory effort, the ventilator may provide the recommendation: "Consider: (1) causes for increased patient inspiratory effort; (2) reducing set $P_{SUPP}$." During VC, VC+ or VS ventilation, when high-delivered $V_T$ is detected concurrent with an increase in patient inspiratory effort, the ventilator may provide the recommendation: "Consider: (1) causes for increased patient inspiratory effort; (2) increasing set $V_T$." During proportional assist (PA) ventilation, when high-delivered $V_T$ is detected concurrent with an increase in patient inspiratory effort, the ventilator may provide the recommendation: "Consider causes for increased patient inspiratory effort,"

At display smart prompt operation 414, the ventilator may alert the clinician via any suitable means that high-delivered $V_T$ was detected. For example, according to embodiments, a smart prompt may include an appropriate primary prompt and an appropriate secondary prompt. Additionally or alternatively, the appropriate primary prompt may include an appropriate notification message that high-delivered $V_T$ was detected and may include the one or more potential causes for the high-delivered $V_T$. According to alternative embodiments, the notification message may be separately displayed from the one or more potential causes for the high-delivered $V_T$. According to this embodiment, the notification message may be initially displayed and the one or more potential causes may be optionally displayed upon selection or activation by the clinician. According to further embodiments, the appropriate secondary prompt may provide the one or more recommendations for addressing the high-delivered $V_T$. According to some embodiments, the appropriate primary prompt may be initially displayed and the appropriate secondary prompt may be optionally displayed upon selection or activation by a clinician. The smart prompt (including the appropriate primary prompt and/or the appropriate secondary prompt) may be displayed via any suitable means, e.g., on the ventilator GUI and/or at a remote monitoring station, such that the clinician is alerted as to the occurrence of high-delivered $V_T$ and/or offered additional information regarding one or more potential causes for the high-delivered $V_T$ and/or offered one or more recommendations for addressing the high-delivered $V_T$, as described herein.

Ventilator GUI Display of Smart Prompt

Figure 5:
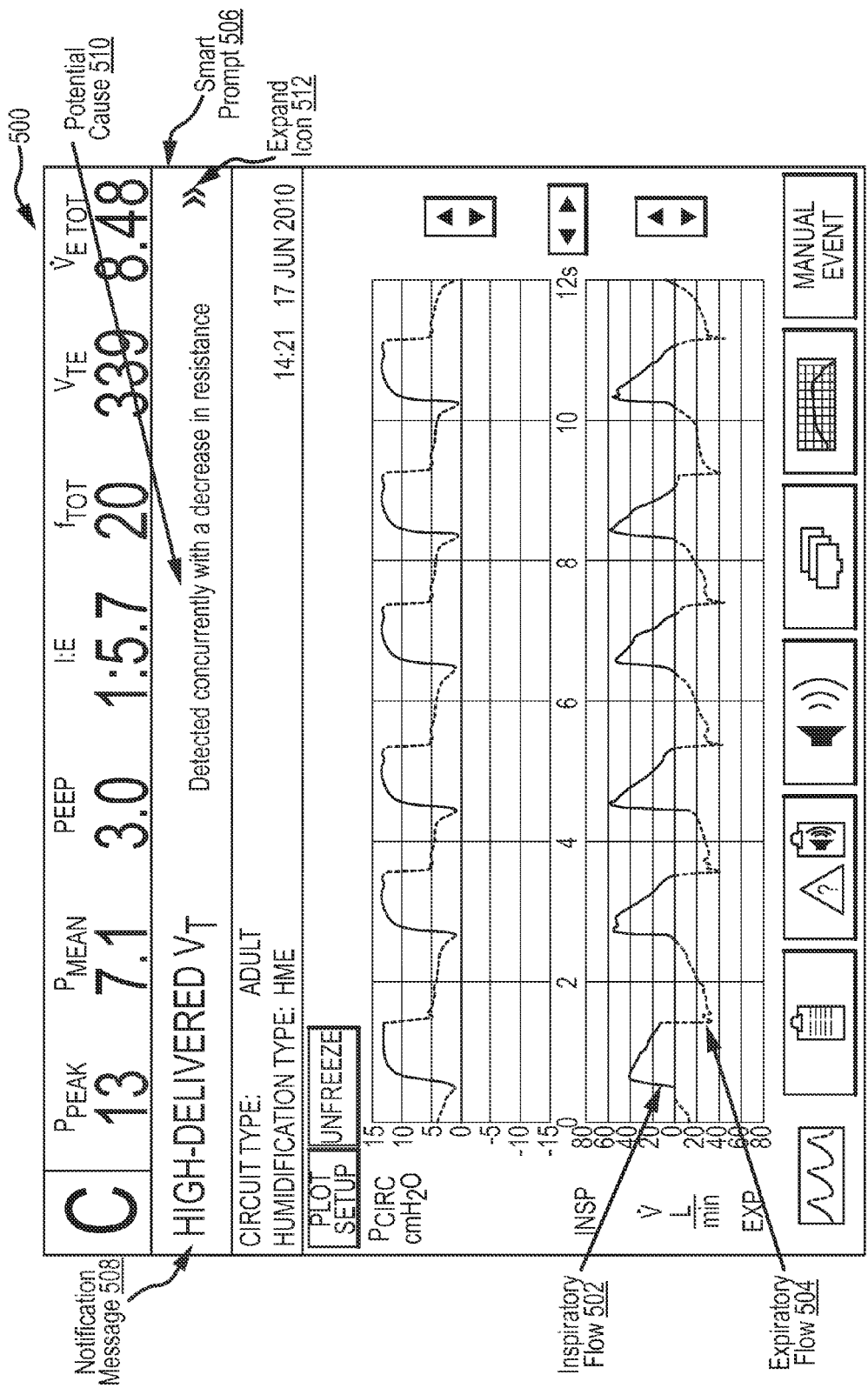
FIG. 5 is an illustration of an embodiment of a graphical user interface displaying a smart prompt element in a window having a notification regarding high-delivered $V_T$ and regarding a potential cause for the high-delivered $V_T$.

FIG. 5 is an illustration of an embodiment of a graphical user interface displaying a smart prompt element in a window having a notification regarding high-delivered $V_T$ and regarding a potential cause for the high-delivered $V_T$.

Graphical user interface 500 may display various monitored and/or derived data to the clinician during ventilation of a patient. In addition, graphical user interface 500 may display various messages to the clinician (e.g., alarm messages, etc.). Specifically, graphical user interface 500 may display a smart prompt as described herein.

According to embodiments, the ventilator may monitor and evaluate various ventilatory parameters to detect high-delivered $V_T$. As illustrated, a flow waveform may be generated and displayed by the ventilator on graphical user interface 500. As further illustrated, the flow waveform may be displayed such that inspiratory flow 502 is represented in a different color (e.g., green) than expiratory flow 504 (e.g., yellow). According to embodiments, delivered $V_T$ may be determined at the end of inspiration, i.e., by integrating inspiratory flow over $T_I$ (either set $T_I$ or patient-determined $T_I$). Alternatively, expiratory flow may be monitored such that exhaled tidal volume ($V_{TE}$) may be derived by integrating expiratory flow over expiratory time ($T_E$). Indeed, delivered $V_T$ may be determined via any suitable means, either currently known or developed in the future. According to embodiments, delivered $V_T$ may be compared to a threshold $V_T$ and, when delivered $V_T$ is greater than the threshold $V_T$, the ventilator may detect high-delivered $V_T$. According to some embodiments, when delivered $V_T$ is greater than the threshold $V_T$ for a period of time or over a number of breaths, the ventilator may detect high-delivered $V_T$.

According to embodiments, smart prompt 506 may be displayed in any suitable location such that a clinician may be alerted regarding a detected patient condition, but while allowing other ventilatory displays and data to be visualized substantially simultaneously. As illustrated, smart prompt 506 is presented as a bar or banner across an upper region of the graphical user interface 500. However, as previously noted, smart prompt 506 may be displayed as a tab, icon, button, banner, bar, or any other suitable shape or form. Further, smart prompt 506 may be displayed in any suitable location within the graphical user interface 500. For example, smart prompt 506 may be located along any border region of the graphical user interface 500 (e.g., top, bottom, or side borders) (not shown), across an upper region (shown), or in any other suitable location. Further, as described herein, smart prompt 506 may be partially transparent (not shown) such that ventilatory displays and data may be at least partially visible behind smart prompt 506.

Specifically, smart prompt 506 may alert the clinician that high-delivered $V_T$ has been detected, for example by notification message 508. As described herein, notification message 508 may alert the clinician that high-delivered $V_T$ was detected via any suitable means, e.g., "High-Delivered $V_T$" (shown) or "High-Delivered $V_T$ Detected" (not shown). Smart prompt 506 may further include information regarding one or more potential causes for high-delivered $V_T$, e.g., potential cause 510. For example, if high-delivered $V_T$ was detected concurrent with a decrease in resistance, this information may be provided to the clinician (e.g., "Detected concurrently with a decrease in resistance," shown). Alternatively, additional information regarding a potential cause may be provided to the clinician (e.g., "Detected concurrently with a 25% decrease in resistance," not shown; or "Detected concurrently with a 25% decrease in resistance from start of ventilation," not shown). According to the illustrated embodiment, potential cause 510 is provided along with the notification message 508 in a banner. According to embodiments the illustrated embodiment may correspond to a primary prompt. According to alternative embodiments, in addition to the notification message 508 and the potential cause 510, one or more recommendations may be provided in an initial smart prompt banner (not shown). According to other embodiments, rather than providing information regarding one or more potential causes for high-delivered $V_T$ in the initial smart prompt (e.g., primary prompt), this information may be provided within an expanded portion (e.g., secondary prompt, not shown) of smart prompt 506.

According to embodiments, smart prompt 506 may be expanded to provide additional information and/or recommendations to the clinician regarding a detected patient condition. For example, an expand icon 512 may be provided within a suitable area of the smart prompt 506. According to embodiments, upon selection of the expand icon 512 via any suitable means, the clinician may optionally expand the smart prompt 506 to acquire additional information and/or recommendations for addressing the detected patient condition. According to further embodiments, smart prompt 506 may include links (not shown) to additional settings and/or display screens of the graphical user interface 500 such that the clinician may easily and quickly address and/or verify the detected condition.

As may be appreciated, the disclosed data, graphics, and smart prompt illustrated in graphical user interface 500 may be arranged in any suitable order or configuration such that information and alerts may be communicated to the clinician in an efficient and orderly manner. The disclosed data, graphics, and smart prompt are not to be understood as an exclusive array, as any number of similar suitable elements may be displayed for the clinician within the spirit of the present disclosure. Further, the disclosed data, graphics, and smart prompt are not to be understood as a necessary array, as any number of the disclosed elements may be appropriately replaced by other suitable elements without departing from the spirit of the present disclosure. The illustrated embodiment of the graphical user interface 500 is provided as an example only, including potentially useful information and alerts that may be provided to the clinician to facilitate communication of detected high-delivered $V_T$ in an orderly and informative way, as described herein.

Ventilator GUI Display of Expanded Smart Prompt

Figure 6:
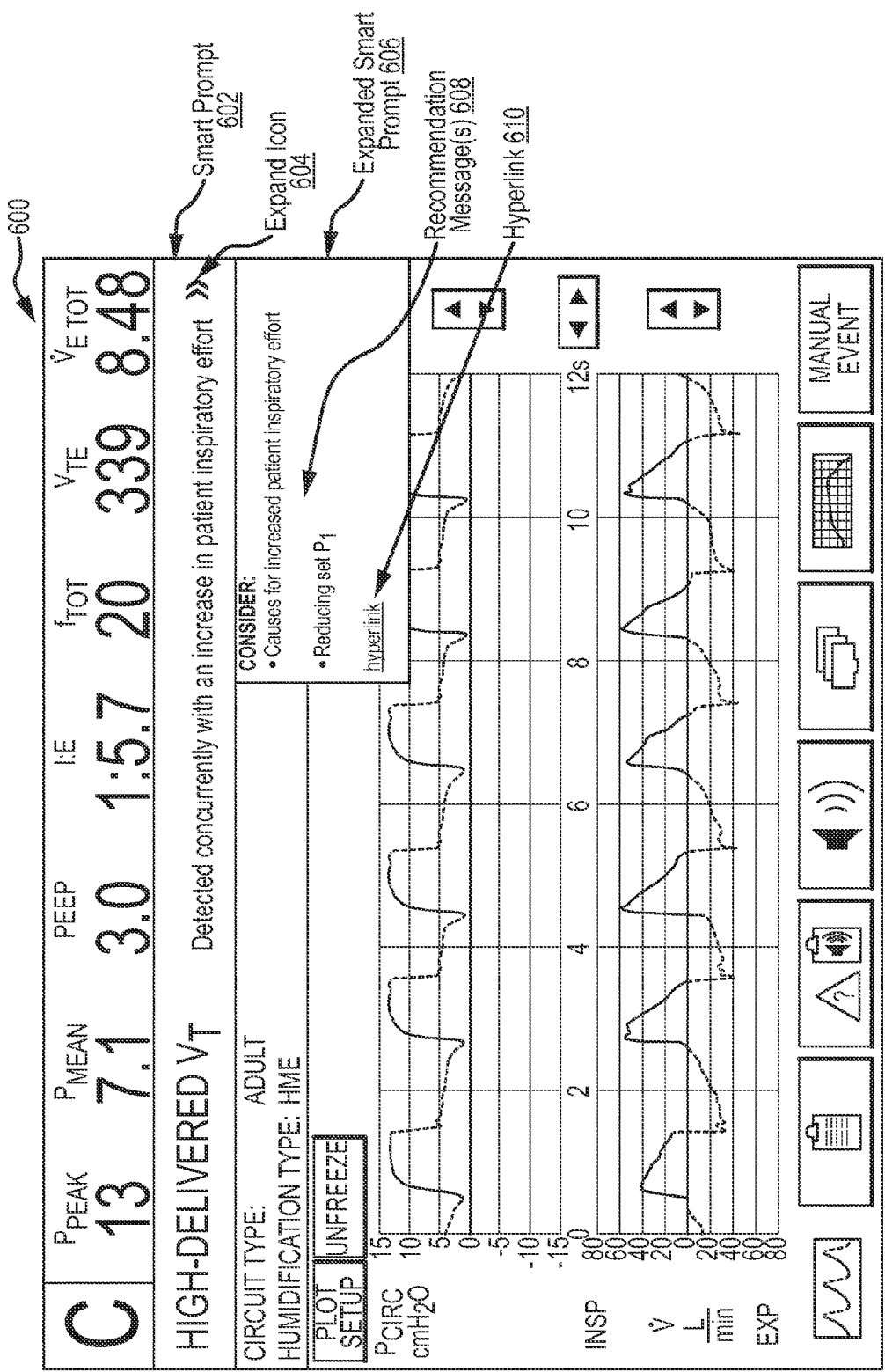
FIG. 6 is an illustration of an embodiment of a graphical user interface displaying an expanded smart prompt element in a window having a notification message regarding high-delivered $V_T$ and a recommendation message regarding addressing the high-delivered $V_T$.

FIG. 6 is an illustration of an embodiment of a graphical user interface displaying an expanded smart prompt element in a window having a notification message regarding high-delivered $V_T$ and a recommendation message regarding addressing the high-delivered $V_T$.

Graphical user interface 600 may display various monitored and/or derived data to the clinician during ventilation of a patient. In addition, graphical user interface 600 may display an expanded smart prompt including one or more recommendation messages, as described herein.

According to embodiments, as described above, an expand icon 604 may be provided within a suitable area of a smart prompt 602. Upon selection of the expand icon 604, the clinician may optionally expand smart prompt 602 to acquire additional information and/or recommendations for addressing the detected patient condition. For example, expanded smart prompt 606 may be provided upon selection of expand icon 604. As described above for smart prompt 506, expanded smart prompt 606 may be displayed as a tab, icon, button, banner, bar, or any other suitable shape or form. Further, expanded smart prompt 606 may be displayed in any suitable location within the graphical user interface 600. For example, expanded smart prompt 606 may be displayed below (shown) smart prompt 602, to a side (not shown) of smart prompt 602, or otherwise logically associated with smart prompt 602. According to other embodiments, an initial smart prompt may be hidden (not shown) upon displaying expanded smart prompt 606. Expanded smart prompt 606 may also be partially transparent (not shown) such that ventilatory displays and data may be at least partially visible behind expanded smart prompt 606. According to some embodiments, expanded smart prompt 606 corresponds to a secondary prompt.

According to embodiments, expanded smart prompt 606 may comprise additional information (not shown) and/or one or more recommendation messages 608 for addressing high-delivered $V_T$. For example, the one or more recommendation messages 608 may be based on a type of ventilation (e.g., VC, PC, PS, VC+, VS, or PA ventilation) being delivered to the patient. Furthermore, the one or more recommendation messages 608 may be based on one or more potential causes for the high-delivered $V_T$.

For example, during PC ventilation (shown), when high-delivered $V_T$ was detected concurrent with an increase in compliance or a decrease in resistance (not shown), the ventilator may provide the recommendation: "Consider reducing set $P_I$." Alternatively, when high-delivered $V_T$ was detected concurrent with an increase in patient inspiratory effort (shown), the ventilator may provide the recommendation: "Consider: (1) causes for increased patient inspiratory effort; (2) reducing set $P_I$."

During PS ventilation (not shown), when high-delivered $V_T$ was detected concurrent with an increase in compliance or a decrease in resistance, the ventilator may provide the recommendation: "Consider reducing set $P_{SUPP}$." Alternatively, when high-delivered $V_T$ was detected concurrent with an increase in patient inspiratory effort, the ventilator may provide the recommendation: "Consider: (1) causes for increased patient inspiratory effort; (2) reducing set $P_{SUPP}$."

During VC ventilation (not shown), VC+ ventilation (not shown) or VS ventilation (not shown), when high-delivered $V_T$ was detected concurrent with an increase in patient inspiratory effort, the ventilator may provide the recommendation: "Consider: (1) causes for increased patient inspiratory effort; (2) increasing set $V_T$."

During PA ventilation (not shown), when high-delivered $V_T$ was detected concurrent with an increase in patient inspiratory effort, the ventilator may provide the recommendation: "Consider causes for increased patient inspiratory effort."

According to embodiments, expanded smart prompt 606 may also include one or more hyperlinks 610, which may provide immediate access to the display and/or settings screens associated with detected high-delivered $V_T$. For example, associated parameter settings screens may be accessed from expanded smart prompt 606 via hyperlink 610 such that the clinician may address detected high-delivered $V_T$ by adjusting one or more parameter settings as necessary. For example, hyperlink 610 may be linked to a setup screen such that the clinician may reduce the set $P_I$ or set $P_{SUPP}$, may increase the set $V_T$, etc. Alternatively, associated parameter display screens may be accessed such that the clinician may view clinical data associated with high-delivered $V_T$ in the form of charts, graphs, or otherwise. That is, according to embodiments, the clinician may access the ventilatory data that implicated one or more potential causes for the high-delivered $V_T$ (e.g., for verification purposes or otherwise). For example, hyperlink 610 may be linked to one or more parameter display screens for evaluating causes for increased inspiratory drive, for evaluating ventilatory data implicating a decrease in resistance, for evaluating ventilatory data implicating an increase in compliance, etc.

As may be appreciated, the disclosed smart prompt and recommendation messages illustrated in graphical user interface 600 may be arranged in any suitable order or configuration such that information and alerts may be communicated to the clinician in an efficient and orderly manner. Indeed, the illustrated embodiment of the graphical user interface 600 is provided as an example only, including potentially useful information and recommendations that may be provided to the clinician to facilitate communication of suggestions for addressing detected high-delivered $V_T$ in an orderly and informative way, as described herein.

Unless otherwise indicated, all numbers expressing measurements, dimensions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. Further, unless otherwise stated, the term "about" shall expressly include "exactly," consistent with the discussions regarding ranges and numerical data. Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 4 percent to about 7 percent" should be interpreted to include not only the explicitly recited values of about 4 percent to about 7 percent, but also include individual values and sub-ranges within the indicated range. Thus, included in this numerical range are individual values such as 4.5, 5.25 and 6 and sub-ranges such as from 4-5, from 5-7, and from 5.5-6.5, etc. This same principle applies to ranges reciting only one numerical value. Furthermore, such an interpretation should apply regardless of the breadth of the range or the characteristics being described.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components, in various combinations of hardware and software, and individual functions can be distributed among software applications at either the client or server level. In this regard, any number of the features of the different embodiments described herein may be combined into one single embodiment and alternative embodiments having fewer than or more than all of the features herein described are possible.

While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A ventilator-implemented method for detecting high-delivered tidal volume ($V_T$), the method comprising:
   receiving one or more ventilatory settings, wherein the one or more ventilatory settings include a threshold $V_T$;
   collecting ventilatory data;
   processing the collected ventilatory data, wherein processing the collected ventilatory data includes determining a delivered $V_T$;
   analyzing the delivered $V_T$, comprising comparing the delivered $V_T$ to the threshold $V_T$;
   detecting high-delivered $V_T$, upon determining that the delivered $V_T$ is greater than the threshold $V_T$;
   identifying one or more potential causes for the high-delivered $V_T$, comprising one or more of:
     detecting an increase in compliance concurrently with the high-delivered $V_T$;
     detecting a decrease in resistance concurrently with the high-delivered $V_T$; and
     detecting an increase in patient inspiratory effort concurrently with the high-delivered $V_T$; and
   displaying a smart prompt when high-delivered $V_T$ is detected.

2. The method of claim 1, wherein the delivered $V_T$ is determined by integrating inspiratory flow over inspiratory time ($T_I$).

3. The method of claim 1, wherein the delivered $V_T$ is determined by integrating expiratory flow over expiratory time ($T_E$).

4. The method of claim 1,
   wherein displaying the smart prompt includes displaying the one or more potential causes for the high-delivered $V_T$.

5. The method of claim 1, wherein detecting an increase in compliance comprises:
   retrieving compliance data;
   comparing the compliance data to a compliance threshold; and determining that the compliance data breaches the compliance threshold.

6. The method of claim 1, wherein detecting a decrease in resistance comprises:
   retrieving resistance data;
   comparing the resistance data to a resistance threshold; and
   determining that the resistance data breaches the resistance threshold.

7. The method of claim 1, wherein detecting an increase in patient inspiratory effort comprises:
   retrieving patient effort data;
   comparing the patient effort data to an effort threshold; and
   determining that the patient effort data breaches the effort threshold.

8. The method of claim 1, wherein the smart prompt comprises:
   a primary prompt that includes an alert regarding the high-delivered $V_T$, and the one or more potential causes for the high-delivered $V_T$; and
   a secondary prompt that includes one or more recommendations for addressing the high-delivered $V_T$.

9. The method of claim 4, wherein displaying the smart prompt includes displaying one or more recommendations for addressing the high-delivered $V_T$.

10. A ventilatory system for issuing a smart prompt when high-delivered tidal volume ($V_T$) is detected, comprising:
    at least one processor; and
    at least one memory, communicatively coupled to the at least one processor and containing instructions that, when executed by the at least one processor, cause the ventilatory system to:
    detect high-delivered $V_T$;
    identify one or more potential causes for the high-delivered $V_T$, comprising one or more of:
      detect an increase in compliance concurrently with the high-delivered $V_T$;
      detect a decrease in resistance concurrently with the high-delivered $V_T$; and
      detect an increase in patient inspiratory effort concurrently with the high-delivered $V_T$;
    determine one or more recommendations for addressing the high-delivered $V_T$; and
    display a smart prompt, the smart prompt comprising one or more of:
      an alert regarding the high-delivered $V_T$;
      a notification message displaying the one or more potential causes for the high-delivered $V_T$; and
      a recommendation message displaying the one or more recommendations for addressing the high-delivered $V_T$.

11. The ventilatory system of claim 10, wherein the smart prompt comprises:
    a primary prompt that includes the alert regarding the high-delivered $V_T$, and the notification message displaying the one or more potential causes for the high-delivered $V_T$; and
    a secondary prompt that includes the recommendation message displaying the one or more recommendations for addressing the high-delivered $V_T$.

12. The ventilatory system of claim 10, wherein the notification message displays at least one of: an increase in compliance detected concurrently with the high-delivered $V_T$, and a decrease in resistance detected concurrently with the high-delivered $V_T$, and wherein the recommendation message displays: consider decreasing inspiratory pressure ($P_I$).

13. The ventilatory system of claim 10, wherein the notification message displays at least one of: an increase in compliance detected concurrently with the high-delivered $V_T$, and a decrease in resistance detected concurrently with the high-delivered $V_T$, and wherein the recommendation message displays: consider decreasing pressure support ($P_{SUPP}$).

14. The ventilatory system of claim 10, wherein the notification message displays: an increase in patient inspiratory effort detected concurrently with the high-delivered $V_T$, and wherein the recommendation message comprises one or more of:
    consider causes for the increase in patient inspiratory effort; and
    consider decreasing inspiratory pressure ($P_I$).

15. The ventilatory system of claim 10, wherein the notification message displays: an increase in patient inspiratory effort detected concurrently with the high-delivered $V_T$, and wherein the recommendation message comprises one or more of:
    consider causes for the increase in patient inspiratory effort; and
    consider decreasing pressure support ($P_{SUPP}$).

16. The ventilatory system of claim 10, wherein the notification message displays: an increase in patient inspiratory effort detected concurrently with the high-delivered $V_T$, and wherein the recommendation message comprises one or more of:

consider causes for the increase in patient inspiratory effort; and consider increasing set $V_T$.

17. A graphical user interface of a ventilator for displaying one or more smart prompts corresponding to a detected condition, the graphical user interface communicatively coupled to the ventilator-for accepting commands and for displaying information, the graphical user interface comprising:

at least one window; and one or more elements within the at least one window comprising at least one smart prompt element for communicating information regarding the detected condition and one or more potential causes for the detected condition, wherein the detected condition is high-delivered tidal volume ($V_T$), and wherein the one or more potential causes for the detected condition include one or more of: an increase in compliance, a decrease in resistance, and an increase in patient inspiratory effort.

18. The graphical user interface of claim 17, wherein the at least one smart prompt element further comprises at least one of a notification message and a recommendation message, wherein the notification message comprises an alert associated with the detected high-delivered $V_T$, and wherein the recommendation message comprises one or more recommendations for addressing the detected high-delivered $V_T$.

19. A ventilator processing interface for displaying a smart prompt in response to detecting high-delivered tidal volume ($V_T$), comprising:

means for retrieving at least some ventilatory data;

means for detecting the high-delivered $V_T$;

means for identifying one or more potential causes for the high-delivered $V_T$, comprising one or more of:

means for detecting an increase in compliance concurrently with the high-delivered $V_T$;

means for detecting a decrease in resistance concurrently with the high-delivered $V_T$; and means for detecting an increase in patient inspiratory effort concurrently with the high-delivered $V_T$; and means for displaying the smart prompt comprising a notification message regarding the high-delivered $V_T$, and the one or more potential causes for the high-delivered $V_T$.

20. The ventilator processing interface of claim 19, further comprising:

means for determining one or more recommendations for addressing the high-delivered $V_T$, wherein the smart prompt further comprises a recommendation message regarding the one or more recommendations for addressing the high-delivered $V_T$.

* * * * *